United States Patent
Chopra

(10) Patent No.: US 11,445,988 B2
(45) Date of Patent: Sep. 20, 2022

(54) SYSTEMS AND METHODS FOR USING X-RAY FIELD EMISSION TO DETERMINE INSTRUMENT POSITION AND ORIENTATION

(71) Applicant: Intuitive Surgical Operations, Inc., Sunnyvale, CA (US)

(72) Inventor: Prashant Chopra, Foster City, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 749 days.

(21) Appl. No.: 16/258,304

(22) Filed: Jan. 25, 2019

(65) Prior Publication Data

US 2019/0239831 A1   Aug. 8, 2019

Related U.S. Application Data

(63) Continuation of application No. 14/613,221, filed on Feb. 3, 2015, now abandoned.

(60) Provisional application No. 61/937,360, filed on Feb. 7, 2014.

(51) Int. Cl.
   *A61B 6/12*   (2006.01)
   *A61B 5/06*   (2006.01)
   *A61B 6/00*   (2006.01)
   *A61B 6/02*   (2006.01)
   (Continued)

(52) U.S. Cl.
   CPC .............. *A61B 6/12* (2013.01); *A61B 1/005* (2013.01); *A61B 1/0607* (2013.01); *A61B 5/065* (2013.01); *A61B 6/025* (2013.01); *A61B 6/4057* (2013.01); *A61B 6/547* (2013.01)

(58) Field of Classification Search
   CPC .......... A61B 1/005; A61B 6/547; A61B 5/065
   See application file for complete search history.

(56) References Cited

U.S. PATENT DOCUMENTS

| | | |
|---|---|---|
| 4,096,862 A | 6/1978 | Deluca et al. |
| 7,532,705 B2 | 5/2009 | Yin et al. |
| 7,711,087 B2 | 5/2010 | Mostafavi |
| (Continued) | | |

OTHER PUBLICATIONS

Cheng Y., et al, "Dynamic Radiography Using a Carbon-Nanotube-Based Field-Emission X-Ray Source," Review of Scientific Instruments, 2004, vol. 75 (10), pp. 3264-3267.

(Continued)

*Primary Examiner* — Jason M Ip
(74) *Attorney, Agent, or Firm* — Haynes and Boone, LLP

(57) ABSTRACT

A method comprises determining a predicted pose of an elongate medical device within a patient anatomy. The method further comprises extracting a plurality of reference images from 3-D reference information, wherein the plurality of reference images includes a predicted reference image corresponding to the predicted pose of the elongate medical device. The method comprises capturing an x-ray image of the patient anatomy, wherein the captured x-ray image includes captured x-ray attenuation information. The method further comprises searching for a closest matching reference image between the captured x-ray image and one of the plurality of reference images. The method comprises determining an offset between the captured x-ray image and the closest matching reference image.

19 Claims, 14 Drawing Sheets

(51) Int. Cl.
*A61B 1/005* (2006.01)
*A61B 1/06* (2006.01)

(56) References Cited

U.S. PATENT DOCUMENTS

| | | | |
|---|---|---|---|
| 2009/0024141 A1 | 1/2009 | Stahler et al. | |
| 2011/0087062 A1 | 4/2011 | Hoernig et al. | |
| 2012/0289843 A1 | 11/2012 | Chopra et al. | |
| 2012/0296202 A1* | 11/2012 | Mountney | A61B 8/4416 600/424 |
| 2013/0010923 A1 | 1/2013 | Lee | |
| 2015/0223765 A1 | 8/2015 | Chopra | |

OTHER PUBLICATIONS

Choi H.Y., et al., "Development of New X-Ray Source Based on Carbon Nanotube Field Emission and Application to the Non Destructive Imaging Technology," IEEE Transactions on Nuclear Science, 2009, vol. 56 (3), pp. 1297-1300.

Gomi T., et al., "X-Ray Digital Linear Tomosynthesis Imaging", J. Biomedical Science and Engineering, 2011, vol. 4, pp. 443-453.

Legagneux P., "Carbon Nanotube Cathodes for Microwave and X-Ray Electron Tubes," 8th International Vacuum Electron Sources Conference and Nanocarbon (IVESC), 2010, pp. 86.

Rajaram R., "A Stationary Digital Breast Tomosynthesis System: Design Simulation, Characterization and Image Reconstruction," Dissertation submitted to University of North Carolina at Chapel Hill, 2009, 148 pages.

Ryu J.H., et al., "Development of Carbon Nanotube X-Ray System for Computed Tomography," 25th International Vacuum Nanoelectronics Conference (IVNC), 2012, 2 pages.

Veress S. A., "X-Ray Photogrammetry, State Of The Art", ISPRS Archives—vol. XXVII Part B5, retrieved from the Internet:< URL: http://www.isprs.org/proceedings/XXVII/congress/part5/592_XXVII-part5.pdf> (1988), pp. 592-599.

Vertut, Jean and Phillips Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

SYSTEMS AND METHODS FOR USING X-RAY FIELD EMISSION TO DETERMINE INSTRUMENT POSITION AND ORIENTATION

CLAIM OF PRIORITY

This application is a continuation of and claims the benefit of priority under 35 U.S.C. § 120 to U.S. patent application Ser. No. 14/613,221, filed on Feb. 3, 2015, which claims the benefit of priority under 35 U.S.C. § 119(e) to U.S. Provisional Patent Application Ser. No. 61/937,360, filed on Feb. 7, 2014, which is incorporated by reference herein in its entirety.

FIELD

The present disclosure is directed to systems and methods for tracking a medical device within a patient anatomy during a medical procedure, and more particularly to systems and methods for efficiently tracking a medical device within a patient anatomy using instrument-mounted field emission x-ray devices.

BACKGROUND

Minimally invasive medical techniques are intended to reduce the amount of tissue that is damaged during diagnostic or surgical procedures, thereby reducing patient recovery time, discomfort, and deleterious side effects. Such minimally invasive techniques may be performed through natural orifices in a patient anatomy or through one or more surgical incisions. Through these natural orifices or incisions clinicians may insert surgical instruments to reach a target tissue location. To reach the target tissue location, the minimally invasive surgical instruments may navigate natural or surgically created connected passageways in anatomical systems such as the lungs, the colon, the intestines, the kidneys, the heart, the circulatory system, or the like. Navigational assist systems help the clinician route the surgical instruments and avoid damage to the anatomy. These systems can incorporate the use of position and shape sensors to more accurately describe the shape, pose, and position of the surgical instrument in real space or with respect to pre-procedural or concurrent images. In a dynamic anatomical system and/or in an anatomical region dense with many anatomical passageways, determinations of the position, orientation and pose of an instrument can be imprecise, especially when considered relative to a target tissue volume that is tiny or to passageways to be navigated that are narrow and complex.

SUMMARY

In one aspect, a device is provided that includes a flexible body. A position sensor is located at the flexible body. A field emission x-ray device is located at the flexible body.

In another aspect, a method is provided that includes providing a field emission x-ray device to a distal end portion of a flexible body. The flexible body, the position sensor and the field emission x-ray device are inserted into an anatomical cavity within a patient's anatomy. X-ray radiation is emitted from the x-ray device and is detected at a location outside the anatomical cavity.

In another aspect, a system is provided that includes a flexible body sized and shaped to be inserted within a human body. A detector is configured to capture one or more x-ray images produced using a field emission x-ray device. One or more processors are configured to determine similarity between the captured one or more x-ray images and a reference x-ray image.

In yet another aspect, a method is provided in which a field emission x-ray device is located at a distal end portion of a flexible body. The flexible body and the field emission x-ray device are inserted into an anatomical cavity within a patient's anatomy. X-rays are emitted from the x-ray device. An x-ray image is captured that includes an x-ray attenuation pattern indicative of anatomical structures traversed by the x-ray radiation. A pose is sensed of the distal end portion of the flexible body. A predicted reference x-ray image is selected, as a function of the sensed pose, from a three-dimensional (3-D) reference x-ray image of a portion of a patient's anatomy that includes the anatomical cavity. A search is made for a match between the captured x-ray image and a reference x-ray image obtained from a prescribed region of the three-dimensional (3-D) reference x-ray image about the predicted reference x-ray image.

In still another aspect, multiple x-ray images are captured and are converted to one or more tomosynthesis images. The search involves a search for a match between the one or more tomosynthesis images and a reference x-ray image obtained from the three-dimensional (3-D) reference x-ray image.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DESCRIPTION OF EMBODIMENTS

Figure 1:
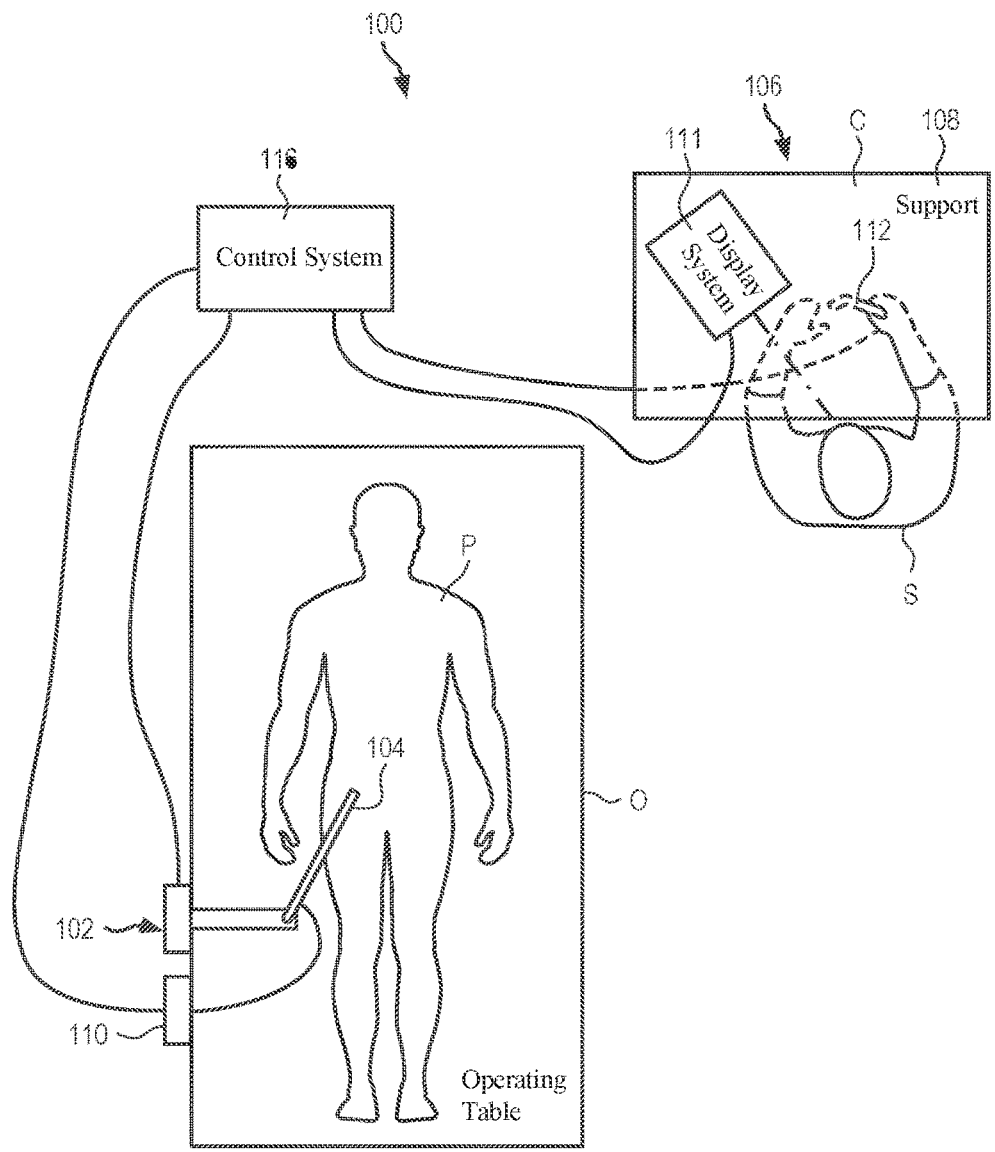
FIG. 1 is an illustrative drawing of a robotic surgical system in accordance with some embodiments.

The following description is presented to enable any person skilled in the art to create and use a system to use field emission x-rays to ascertain and to adjust position and orientation of a flexible robotic medical instrument within an anatomical volume. Various modifications to the embodiments will be readily apparent to those skilled in the art, and the generic principles defined herein may be applied to other embodiments and applications without departing from the spirit and scope of the inventive subject matter. Moreover, in the following description, numerous details are set forth for the purpose of explanation. However, one of ordinary skill in the art will realize that the inventive subject matter might be practiced without the use of these specific details. In other instances, well-known machine components, processes and data structures are shown in block diagram form in order not to obscure the disclosure with unnecessary detail. Identical reference numerals may be used to represent different views of the same item in different drawings. Flow diagrams in drawings referenced below are used to represent processes. A computer system may be configured to perform some of these processes. Modules within flow diagrams representing computer implemented processes represent the configuration of a computer system according to computer program code to perform the acts described with reference to these modules. Thus, the inventive subject matter is not intended to be limited to the embodiments shown, but is to be accorded the widest scope consistent with the principles and features disclosed herein.

Definitions

The embodiments below will describe various instruments and portions of instruments in terms of their state in three-dimensional space.

As used herein, the term "position" refers to the location of an object or a portion of an object in a three-dimensional space (e.g., three degrees of translational freedom along Cartesian X,Y,Z coordinates).

As used herein, the term "orientation" refers to the rotational placement of an object or a portion of an object (three degrees of rotational freedom—e.g., roll, pitch, and yaw).

As used herein, the term "pose" refers to the position of an object or a portion of an object in at least one degree of translational freedom and to the orientation of that object or portion of the object in at least one degree of rotational freedom (up to six total degrees of freedom).

As used herein, the term "shape" refers to a set of poses, positions, or orientations measured along an object.

As used herein, the term "working volume" refers to a volume that is adjacent to an end portion of the medical instrument and that is accessible from the end portion for treatment or diagnosis.

Introduction

In some embodiments, in operation, a medical instrument extends within an anatomical volume within a patient's body. Multiple field emission devices are mounted to an end portion of the instrument and are aligned to emit x-ray radiation that is incident upon a working volume. The working volume changes with changes of position or orientation of the end portion within the anatomical volume. An x-ray detector is disposed in a spaced relation to the end portion and in alignment with radiation beams emitted from the field emission devices so as to capture one or more x-ray images from a viewpoint of the end portion. The radiation beams are attenuated as they pass through body tissue disposed between the emission devices and the detector. The denser the tissue material, the greater will be the attenuation of the beams. The captured x-ray images, which are indicative of a detected actual location of the end portion of the instrument, show beam attenuation patterns that represent structures disposed between the emission devices and the detector from the viewpoint of the end portion. A predicted location of the working volume is determined based at least in part upon sensing of a pose of the instrument. Reference image information corresponding to the predicted pose of the end portion of the instrument, and therefore of the x-ray devices mounted thereon, within the patient's body can be obtained from a 3-D planning image of the patient's body. Captured x-ray image information corresponding to the detected actual location of the end portion is compared with reference x-ray image information corresponding to the predicted pose of the end portion of the instrument. In response to a difference between the actual and predicted pose of the end portion of the instrument, a pose of at least a portion of the instrument is changed to change the working volume.

Robotic Surgical System

FIG. 1 is an illustrative drawing of a robotic surgical system generally indicated by the reference numeral 100, in accordance with some embodiments. The robotic system 100 generally includes a surgical manipulator assembly 102 for controlling operation of a surgical instrument 104 in performing various procedures on a patient P. The assembly 102 is mounted to or near an operating table O. A master assembly 106 allows a surgeon S to view the surgical site and to control the manipulator assembly 102.

In alternative embodiments, the robotic system may include more than one manipulator assembly. The exact number of manipulator assemblies will depend on the surgical procedure and the space constraints within the operating room among other factors.

The master assembly 106 may be located at a surgeon's console C which is usually located in the same room as operating table O. However, it should be understood that the surgeon S can be located in a different room or a completely different building from the patient P. Master assembly 106 generally includes an optional support 108 and one or more control device(s) 112 for controlling the manipulator assembly 102. The control device(s) 112 may include any number of a variety of input devices, such as joysticks, trackballs, gloves, trigger-guns, hand-operated controllers, voice recognition devices or the like. In some embodiments, the control device(s) 112 will be provided with the same degrees of freedom as the associated surgical instruments 104 to provide the surgeon S with telepresence, or the perception that the control device(s) 112 are integral with the instrument 104 so that the surgeon S has a strong sense of directly controlling instrument 104. In some embodiments, the control device(s) 112 is a manual input device which moves with six degrees of freedom, and which may also include an actuatable handle for actuating instruments (for example, for closing grasping jaws, applying an electrical potential to an electrode, delivering a medicinal treatment, or the like).

A visualization system 110 provides a concurrent two or three dimensional image of a surgical site to surgeon console C. The visualization system 110 may include a viewing scope assembly (described in greater detail below) such that a concurrent or real-time visual image of a surgical site is provided to surgeon console C. In some embodiments, visual images also may be captured by an endoscope positioned within the surgical site. In some embodiments, the visualization system 110 includes x-ray field emission components that may be integrally or removably coupled to the surgical instrument 104 such that a concurrent x-ray image of a surgical site is provided to surgeon console C. In alternative embodiments, a separate endoscope, attached to a separate manipulator assembly, may be used with the surgical instrument 104 to image the surgical site. The visualization system 110 may be implemented as hardware, firmware, software or a combination thereof which interact with or are otherwise executed by one or more computer processors, which may include the processors of a control system 116 (described below).

A display system 111 may display a visual image of the surgical site and surgical instruments 104 captured by the visualization system 110. The display system 111 and the master control devices 112 may be oriented such that the relative positions of the visual imaging device in the scope assembly and the surgical instruments 104 are similar to the relative positions of the surgeon's eyes and hands so the operator can manipulate the surgical instrument 104 and the hand control as if viewing a working volume adjacent to the instrument 104 in substantially true presence. By "true presence" it is meant that the presentation of an image is a true perspective image simulating the viewpoint of an operator that is physically manipulating the surgical instruments 104.

Alternatively or additionally, display system 111 may present images of the surgical site recorded and/or modeled preoperatively using imaging technology such as computerized tomography (CT), magnetic resonance imaging (MRI), fluoroscopy, thermography, ultrasound, optical coherence tomography (OCT), thermal imaging, impedance imaging, laser imaging, or nanotube X-ray imaging. The presented preoperative images, also referred to as "planning images", may include two-dimensional, three-dimensional, or four-dimensional images. In some embodiments, the display system 111 may display a virtual navigational image in which the current location of the surgical instrument 104 is registered (i.e., dynamically referenced) with preoperative or concurrent images to present the surgeon S with a virtual image of the internal surgical site at the location of an end portion of the surgical instrument 104. An image of the end portion of the surgical instrument 104 or other graphical or alphanumeric indicators may be superimposed on the virtual image to assist the surgeon S in controlling the surgical instrument 104. Alternatively, the surgical instrument 104 may not be visible in the virtual image.

In other embodiments, the display system 111 may display a virtual navigational image in which the current location of the surgical instrument 104 is registered with preoperative or concurrent images to present the surgeon S with a virtual image of the surgical instrument 104 within the surgical site from an external viewpoint. An image of a portion of the surgical instrument 104 or other graphical or alphanumeric indicators may be superimposed on the virtual image to assist the surgeon S in controlling the surgical instrument 104.

As shown in FIG. 1, a control system 116 includes at least one processor (not shown) and typically a plurality of processors for effecting control between the surgical manipulator assembly 102, the master assembly 106, and the display system 110. The control system 116 also includes software programming instructions to implement some or all of the methods described herein. While control system 116 is shown as a single block in the simplified schematic of FIG. 1, the control system 116 may comprise a number of data processing circuits (e.g., on the surgical manipulator assembly 102 and/or on the master assembly 106), with at least a portion of the processing optionally being performed adjacent an input device, a portion being performed adjacent a manipulator, and the like. Any of a wide variety of centralized or distributed data processing architectures may be employed. Similarly, the programming code may be implemented as a number of separate programs or subroutines, or may be integrated into a number of other aspects of the robotic systems described herein. In one embodiment, control system 116 may support wireless communication protocols such as Bluetooth, IrDA, HomeRF, IEEE 802.11, DECT, and Wireless Telemetry.

In some embodiments, control system 116 may include servo controllers to provide force and torque feedback from the surgical instrument 104 to the hand-operated control device 112. Any suitable conventional or specialized servo controller may be used. A servo controller may be separate from, or integral with, manipulator assembly 102. In some embodiments, the servo controller and manipulator assembly 102 are provided as part of a robotic arm cart positioned adjacent to the patient's body. The servo controllers transmit signals instructing the manipulator assembly 102 to move the instrument 104, which extends into an internal surgical site within the patient body via openings in the body. Each manipulator assembly 102 supports a surgical instrument 104 and may comprise a series of manually articulatable linkages, generally referred to as set-up joints, and a robotic manipulator. The manipulator assembly 102 may be driven by a series of actuators (e.g., motors). These motors actively move the robotic manipulators in response to commands from the control system 116. The motors are further coupled to the surgical instrument 104 so as to advance the surgical instrument 104 into a naturally or surgically created anatomical orifice and to move the surgical instrument 104 in multiple degrees of freedom that may include three degrees of linear motion (e.g., X, Y, Z linear motion) and three degrees of rotational motion (e.g., roll, pitch, yaw). Additionally, the motors can be used to actuate an effector of the surgical instrument 104 such as an articulatable effector for grasping tissues in the jaws of a biopsy device or an effector for obtaining a tissue sample or for dispensing medicine, or another effector for providing other treatment as described more fully below, for example.

Tracked Instrument System

Figure 2A:
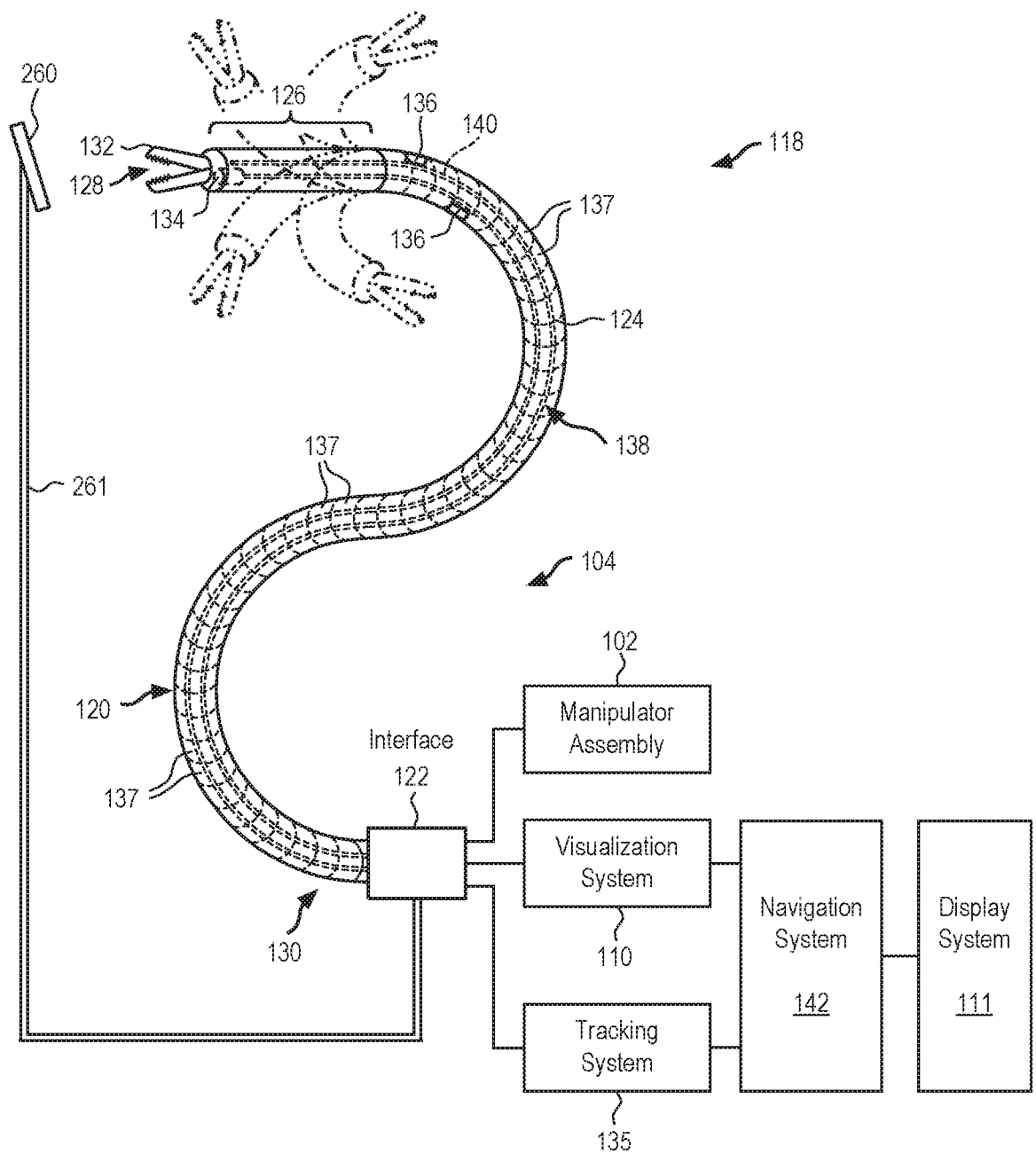
FIG. 2A is an illustrative drawing representing a tracked instrument system which includes the surgical instrument system of FIG. 1 and its interfacing systems in accordance with some embodiments.

FIG. 2A is an illustrative drawing representing a tracked instrument system 118 which includes the robotic system 100 of FIG. 1 and its interfacing systems in accordance with some embodiments. The tracked instrument system 118 includes a flexible instrument 120 coupled by an electro-optical communications interface 122 to the manipulator assembly 102 and visualization system 110. The interface 122 includes circuitry and/or fiber optics configured to communicate control signals and information-containing signals, such as electrical signals indicating the disposition of an end effector 132 and optical signals indicating instrument shape, between the manipulator assembly 102 and the flexible instrument 120. The interface 122 also includes circuitry and/or fiber optics configured to communicate control signals and information-containing signals, such as signals indicating a captured image, between the visualization system 110 and the flexible instrument 120. The flexible instrument 120 includes an elongated flexible body 124, an end portion 126 at its distal end 128, and the interface 122 at its proximal end 130. The body 124 houses cables, linkages, or other steering controls (not shown) that extend between the interface 122 and the end portion 126 to controllably bend or turn the end portion 126 as shown for example by the dotted line versions of the end portion 126, and in some embodiments control an optional end effector 132.

The flexible instrument 120 may be steerable, including the steering controls previously described, or may be non-steerable with no integrated mechanism for operator control of the flexible instrument 120 bending. The end effector 132 may be a working distal part that is manipulable for a medical function, e.g., for effecting a predetermined treatment of a target tissue. For instance, some end effectors have a single working member such as a scalpel, a blade, or an electrode. Other end effectors, such as end effector 132 shown in the embodiment of FIG. 2A, have a pair or plurality of working members such as forceps, graspers, scissors, or clip appliers, for example. Examples of electrically activated end effectors include electrosurgical electrodes, transducers, sensors, and the like. End effectors may also include conduits to convey fluids, gases or solids to perform, for example, suction, insufflation, irrigation, certain treatments requiring fluid delivery, accessory introduction, biopsy extraction, and the like. In other embodiments, the flexible body 124 can define one or more lumens through which surgical instruments can be deployed and used at a target surgical location.

The flexible instrument 120 can also include an image capture element 134, which may include a stereoscopic or monoscopic camera disposed at the distal end 128 for capturing images that are transmitted to and processed by the visualization system 110 for display by the display system 111. Alternatively, the image capture element 134 may include a coherent fiber-optic bundle that couples to an imaging and processing system on the proximal end 130 of the flexible instrument 120, such as a fiberscope. The image capture element 134 may be single or multi-spectral for capturing image data in the visible or infrared/ultraviolet spectrum.

Figure 2B:
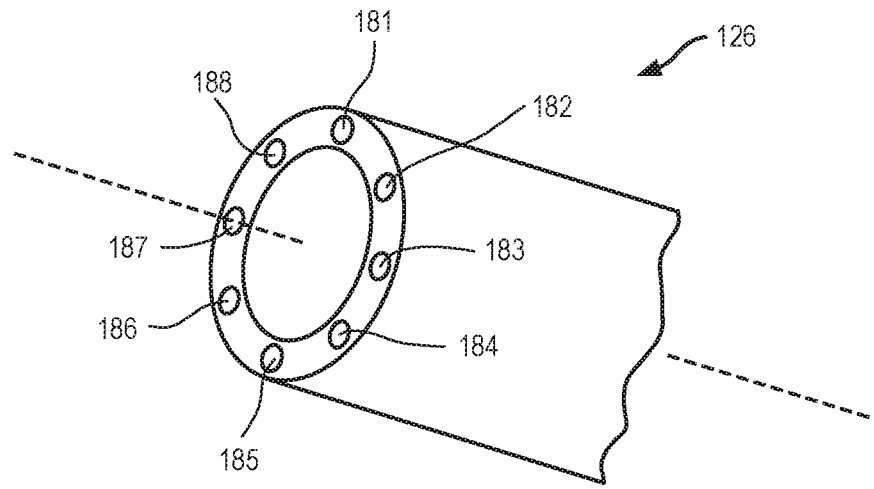
FIG. 2B provides an illustrative perspective view of the end portion, which includes multiple field emission x-ray devices used to generate information in the form of 2-D projection images that are indicative of the location of a working volume in accordance with some embodiments.

FIG. 2B provides an illustrative perspective view of the end portion 126, which includes multiple field emission x-ray devices 181-188 used to generate information in the form of 2-D projection images that are indicative of the location of a working volume in accordance with some embodiments. The end portion 126 has a center axis 190, which extends along a Z-direction, and the field emission x-ray devices 181-188 are secured to the end portion 126, either integrally or removably, about the center axis 190. The x-ray emissions emitted by the x-ray devices 181-188 are attenuated as they pass through the patient body and are captured as 2-D x-ray projection images by one or more x-ray detectors 260 (of FIGS. 4A-4D) mounted on structure 261. The 2-D projection images provide information concerning the structure and density of body tissue disposed between the end portion 126 and an x-ray detector (not shown), which can be used to determine the location of the working volume. More particularly, information from the 2-D projection images is processed by the visualization system 110 for use in generating a display by the display system 111 to provide an indication of the location, orientation and/or pose of the end portion 126, and therefore, of the x-ray devices 181-188 mounted thereon. Information concerning the location orientation and/or pose of the end portion 126 determined using the 2-D projection images can be compared with planning images to aid a surgeon in manipulating the surgical instrument 104 so as to guide the end portion 126 to bring the working volume into alignment with an intended target volume.

In some embodiments, the field emission x-ray devices 181-188 include carbon nanotubes (CNTs) that are configured to act as electron emission sources for the production of x-ray radiation. Field emission involves extraction of electrons from a conducting solid by an electric field. In general, relatively high electric fields are needed for the electrons to tunnel through a surface potential barrier and to achieve field emission. However, when the solid is shaped as a sharp tip, the electric field lines are concentrated around the tip and the local electric field is enhanced. This geometrical enhancement of the electric field is used in field emitters to allow extraction of electrons from sharp tips at relatively low macroscopic electric fields. CNTs are among the sharpest and strongest materials known, and as a result, they are effective materials for use as field emission x-ray devices, also referred to as cathodes. It will be appreciated that since field emission of electrons is produced by a high electric field, no heating is necessary. Field emission sources are thus often referred to as cold cathode sources. Beneficially, the electron beams emitted by a field emission source may have low divergence and thus provide ease of focusing onto a focal spot. Moreover, the virtually instantaneous response of a typical field emission source to an electric field results in rapid switching capabilities that sometimes may even be on the order of nanoseconds, for example. Furthermore, because field emission sources can be made exceedingly small, field emission x-ray sources are highly amenable to formation into arrays that comprise multiple sources. Further discussions of carbon nanotube based field-emission x-ray sources are provided by Chang et al., "Dynamic radiography using a carbon-nanotube-based field-emission," Review of Scientific Instruments, Volume 75, No. 10, October 2004; and Choi et al., "Development of New X-Ray Source Based on Carbon Nanotube Field Emission and Application to the Non Destructive Imaging Technology," IEEE Transactions on Nuclear Science, Vol. 56, No. 3, June 2009.

Referring again to FIG. 2A, a tracking system 135 includes an electromagnetic (EM) sensor system 136 and a shape sensor system 138 for determining the position, orientation, speed, pose, and/or shape of the distal end portion 126 and of one or more segments 137 along the flexible instrument 120. Although only an exemplary set of segments 137 is depicted in FIG. 2A, the entire length of the body 124, between the distal end 128 and the proximal end 130, and including the end portion 126, may be effectively divided into segments such that the body 124 is articulable at segment boundaries. The tracking system 135 may be implemented as hardware, firmware, software or a combination thereof, which interact with or are otherwise executed by one or more computer processors, which may include the processors of the control system 116.

The EM sensor system 136 includes one or more conductive coils that may be subjected to an externally generated electromagnetic field. Each coil of the EM sensor system 136 then produces an induced electrical signal having characteristics that depend on the position and orientation of the coil relative to the externally generated electromagnetic field. In one embodiment, the EM sensor system 136 may be configured and positioned to measure six degrees of freedom, e.g., three position coordinates X, Y, Z and three orientation angles indicating pitch, yaw, and roll of a base point. Further description of an EM sensor system is provided in U.S. Pat. No. 6,380,732, filed Aug. 11, 1999, disclosing "Six-Degree of Freedom Tracking System Having a Passive Transponder on the Object Being Tracked," which is incorporated by reference herein in its entirety.

The shape sensor system 138 includes an optical fiber 140 aligned with the flexible body 124 (e.g., provided within an interior channel (not shown) or mounted externally). The tracking system 135 is coupled to a proximal end of the optical fiber 140. In this embodiment, the fiber 140 has a diameter of approximately 200 µm. In other embodiments, the dimensions may be larger or smaller.

The optical fiber 140 forms a fiber optic bend sensor for determining the shape of the flexible instrument 120. In one alternative, optical fibers including Fiber Bragg Gratings (FBGs) are used to provide strain measurements in structures in one or more dimensions. Various systems and methods for monitoring the shape and relative position of an optical fiber in three dimensions are described in U.S. patent application Ser. No. 11/180,389, filed Jul. 13, 2005, (now abandoned) disclosing "Fiber optic position and shape sensing device and method relating thereto" claiming benefit of U.S. Provisional Pat. App. No. 60/588,336 and U.S. Pat. No. 6,389,187, filed on Jun. 17, 1998, disclosing "Optical Fibre Bend Sensor," which are incorporated by reference herein in their entireties. In other alternatives, sensors employing other strain sensing techniques such as Rayleigh scattering, Raman scattering, Brillouin scattering, and Fluorescence scattering may be suitable. In other alternative embodiments, the shape of the flexible instrument 120 may be determined using other techniques. For example, if the history of the flexible instrument tip's pose is stored for an interval of time that is smaller than the period for refreshing the navigation display or for alternating motion (e.g., inhalation and exhalation), the pose history can be used to reconstruct the shape of the flexible instrument 120 over the interval of time. As another example, historical pose, position, or orientation data may be stored for a known point of flexible instrument 120 along a cycle of alternating motion, such as breathing. This stored data may be used to develop shape information about the flexible instrument 120. Alternatively, a series of positional sensors, such as EM sensors 136, positioned along the flexible instrument 120 can be used for shape sensing. Alternatively, a history of data from a positional sensor, such as an EM sensor 136, on the flexible instrument 120 during a procedure may be used to represent the shape of the flexible instrument 120, particularly if an anatomical passageway is generally static. Alternatively, a wireless device with position or orientation controlled by an external magnetic field may be used for shape sensing. The history of its position may be used to determine a shape for the navigated passageways.

In this embodiment, the optical fiber 140 may include multiple cores within a single cladding. Each core may be single-mode with sufficient distance and cladding separating the cores such that the light in each core does not interact significantly with the light carried in other cores. In other embodiments, the number of cores may vary or each core may be contained in a separate optical fiber.

In some embodiments, an array of FBGs is provided within each core. Each FBG comprises a series of modulations of the core's refractive index so as to generate a spatial periodicity in the refraction index. The spacing may be chosen so that the partial reflections from each index change add coherently for a narrow band of wavelengths, and therefore reflect only this narrow band of wavelengths while passing through a much broader band. During fabrication of the FBGs, the modulations are spaced by a known distance, thereby causing reflection of a known band of wavelengths. However, when a strain is induced on the fiber core, the spacing of the modulations will change, depending on the amount of strain in the core. Alternatively, backscatter or other optical phenomena that vary with bending of the optical fiber can be used to determine strain within each core.

Thus, to measure strain, light is sent down the fiber, and characteristics of the returning light are measured. For example, FBGs produce a reflected wavelength that is a function of the strain on the fiber and its temperature. This FBG technology is commercially available from a variety of sources, such as Smart Fibres Ltd. of Bracknell, England. Use of FBG technology in position sensors for robotic surgery is described in U.S. Pat. No. 7,930,065, filed Jul. 20, 2006, disclosing "Robotic Surgery System Including Position Sensors Using Fiber Bragg Gratings," which is incorporated by reference herein in its entirety.

When applied to a multicore fiber, bending of the optical fiber induces strain on the cores that can be measured by monitoring the wavelength shifts in each core. By having two or more cores disposed off-axis in the fiber, bending of the fiber induces different strains on each of the cores. These strains are a function of the local degree of bending of the fiber. For example, regions of the cores containing FBGs, if located at points where the fiber is bent, can thereby be used to determine the amount of bending at those points. These data, combined with the known spacings of the FBG regions, can be used to reconstruct the shape of the fiber. Such a system has been described by Luna Innovations. Inc. of Blacksburg, Va.

As described, the optical fiber 140 is used to monitor the shape of at least a portion of the flexible instrument 120. More specifically, light passing through the optical fiber 140 is processed by the tracking system 135 for detecting the shape of the flexible instrument 120 and for utilizing that information to assist in surgical procedures. The tracking system 135 may include a detection system for generating and detecting the light used for determining the shape of the flexible instrument 120. This information, in turn, can be used to determine other related variables, such as velocity and acceleration of the parts of a surgical instrument. By obtaining accurate measurements of one or more of these variables in real time, the controller 116 can improve the accuracy of the robotic surgical system and compensate for errors introduced in driving the component parts. The sensing may be limited only to the degrees of freedom that are actuated by the robotic system 100, or may be applied to both passive (e.g., unactuated bending of the rigid members between joints) and active (e.g., actuated movement of the instrument) degrees of freedom.

The information from the tracking system 135 may be sent to the navigation system 142 where it is combined with information from the visualization system 110 and/or the preoperatively taken images to provide the surgeon or other operator with real-time position information on the display system 111 for use in the control of the flexible instrument 120. The control system 116 may utilize the position information as feedback for positioning the instrument 120. Various systems for using fiber optic sensors to register and display an image representing position, orientation and pose of a surgical instrument with surgical images of anatomical features are provided in U.S. patent application Ser. No. 13/107,562, filed May 13, 2011, disclosing, "Medical System Providing Dynamic Registration of a Model of an Anatomical Structure for Image-Guided Surgery," which is incorporated by reference herein in its entirety.

In the embodiment of FIG. 2A, the instrument 104 is teleoperated within the tracked instrument system 118. In an alternative embodiment, the manipulator assembly 102 may be replaced by direct operator control. In the direct operation alternative, various handles and operator interfaces may be included for hand-held operation of the flexible instrument 120.

Tomosynthesis Images from Field Emission X-Rays Produced within the Body

Figure 3:
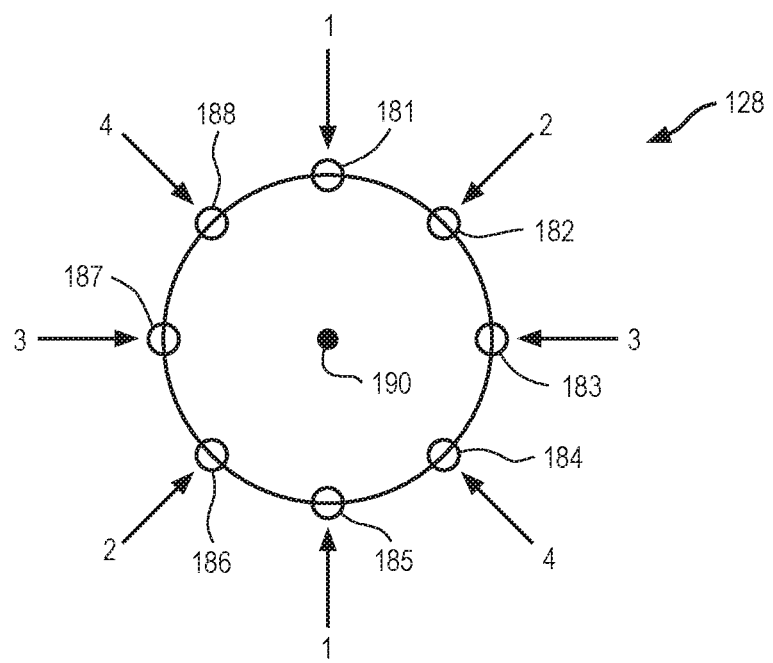
FIG. 3 is a generalized longitudinal end view of the distal end of the end portion showing disposition of multiple x-ray emission devices disposed about a circumference of the end portion in accordance with some embodiments.

FIG. 3 is a generalized longitudinal end view of the distal end 128 of the end portion 126 having center axis 190 showing disposition of multiple field emission x-ray devices 181-188 disposed about a circumference of the end portion 126 in accordance with some embodiments. The end portion 126 is shown as substantially circular in cross-section and has eight emission x-ray devices 181-188 distributed at uniform angular displacements about its circumference, although the end portion 126 need not be circular in cross section and the emission x-ray devices 181-188 need not be uniformly distributed. The x-ray devices 181-188 are oriented to emit electrons in a direction to intersect a working volume as explained more fully below. More particularly, in some embodiments, in order to facilitate tomosynthesis, the x-ray devices 181-188 are oriented so that electrons emitted by the different x-ray devices 181-188 follow paths, which in operation, are incident upon the working volume adjacent to the distal end 128 of the end portion 126.

FIGS. 4A-4D are illustrative cross-sectional side views of the end portion 126 shown in FIG. 3 generally along lines 1-1 (FIG. 4A), lines 2-2 (FIG. 4B), lines 3-3 (FIG. 4C) and lines 4-4 (FIG. 4D) in accordance with some embodiments. X-ray radiation beams 241-248 emitted by the x-ray devices 181-188 are incident upon a tissue volume 230 disposed within the working volume 232 and are incident upon one or more x-ray detectors 260, hereinafter referred to as "detector" 260. The x-ray devices 181-188 can emit radiation in a prescribed sequence, for example. Of course, the x-ray radiation beams 241-248 also pass through additional body tissue while en route between the emission x-ray devices 181-188 and the detector 260. X-ray image detectors are known to persons of ordinary skill in the art and will not be described in detail herein. As explained more fully below, one of the uses of the system and method disclosed herein is to ascertain the location, orientation and/or pose of the end portion 126 within a natural or surgically created anatomical lumen, for example. Another use of the system and method is to determine whether the tissue volume 230 within the working volume 232 comprises a target tissue volume, which is an intended target of diagnosis or treatment, for example.

Figure 4A:
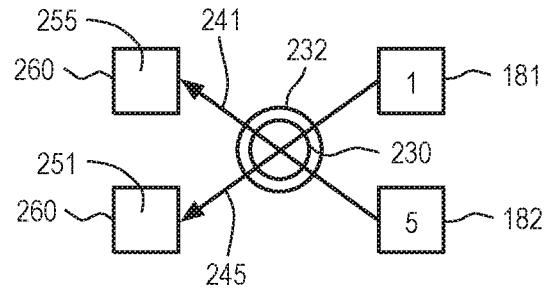
FIGS. 4A-4D are illustrative cross-sectional side views of the distal end portion shown in FIG. 3 in accordance with some embodiments.

FIG. 4A shows a first x-ray radiation beam 241 emitted by a first emission device 182 mounted upon the end portion 126 at a first angular position and configured to aim the first x-ray radiation beam 241 through the tissue volume 230 within the working volume 232 so as to produce a first 2-D x-ray projection image 255 upon a detector 260 that is indicative of objects disposed along a path of the first x-ray radiation beam 241 between the end portion 126 and the x-ray detector 260. FIG. 4A also shows a fifth x-ray radiation beam 245 emitted by a fifth emission device 185 mounted upon the end portion 126 at a fifth angular position and configured to aim the fifth x-ray radiation beam 245 through tissue volume 230 within the working volume 232 so as to produce a fifth x-ray image projection 251 upon the detector 260 that is indicative of objects disposed along a path of the fifth x-ray radiation beam 245 between the end portion 126 and the x-ray detector 260.

Figure 4B:
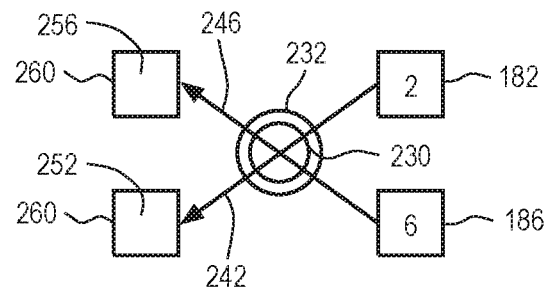

FIG. 4B shows a second x-ray radiation beam 242 emitted by a second emission device 182 mounted upon the end portion 126 at a second angular position configured to aim the second x-ray radiation beam 242 through the tissue volume 230 within the working volume 232 so as to produce a second 2-D x-ray projection image 252 upon the detector 260 that is indicative of objects disposed along a path of the second x-ray radiation beam 242 between the end portion 126 and the x-ray detector 260. FIG. 4B also shows a sixth x-ray radiation beam 246 emitted by a sixth emission device 186 mounted upon the end portion 126 at a sixth angular position and configured to aim a sixth x-ray radiation beam 246 through tissue volume 230 within the working volume 232 so as to produce a sixth x-ray image projection 256 upon the detector 260 that is indicative of objects disposed along a path of the sixth x-ray radiation beam 246 between the end portion 126 and the x-ray detector 260.

Figure 4C:
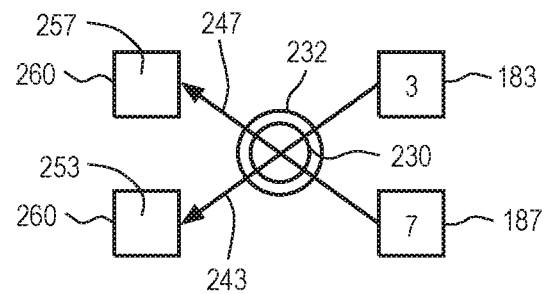

FIG. 4C shows a third x-ray radiation beam 243 emitted by a third emission device 183 mounted upon the end portion 126 at a third angular position and configured to aim the third x-ray radiation beam 243 through the tissue volume 230 within the working volume 232 so as to produce a third 2-D x-ray projection image 253 upon the detector 260 that is indicative of objects disposed along a path of the third x-ray radiation beam 243 between the end portion 126 and the x-ray detector 260. FIG. 4C also shows a seventh x-ray radiation beam 247 emitted by a seventh emission device 187 mounted upon the end portion 126 at a seventh angular position and configured to aim the seventh x-ray radiation beam 247 through tissue volume 230 within the working volume 232 so as to produce a seventh x-ray image projection 257 upon the detector 260 that is indicative of objects disposed along a path of the seventh x-ray radiation beam 247 between the end portion 126 and the x-ray detector 260.

Figure 4D:
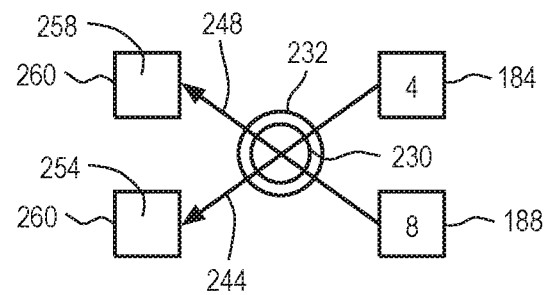

FIG. 4D shows a fourth x-ray radiation beam 244 emitted by a fourth emission device 184 mounted upon the end portion 126 at a fourth angular position 192 and configured to aim the fourth x-ray radiation beam 244 through the tissue volume 230 within the working volume 232 so as to produce a fourth 2-D x-ray projection image 254 upon the detector 260 that is indicative of objects disposed along a path of the fourth x-ray radiation beam 244 between the end portion 126 and the x-ray detector 260. FIG. 4D also shows an eighth x-ray radiation beam 248 emitted by an eighth emission device 188 mounted upon the end portion 126 at an eighth angular position and configured to aim the eighth x-ray radiation beam 248 through tissue volume 230 within the working volume 232 so as to produce an eighth x-ray image projection 258 upon the detector 260 that is indicative of objects disposed along a path of the eighth x-ray radiation beam 248 between the end portion 126 and the x-ray detector 260.

It will be appreciated of course that greater or fewer than eight emission devices 181-188 may be employed and that greater or fewer than eight 2-D x-ray projection images 251-258 may be produced. Also, the angular displacements need not be uniform, for example.

Figure 5:
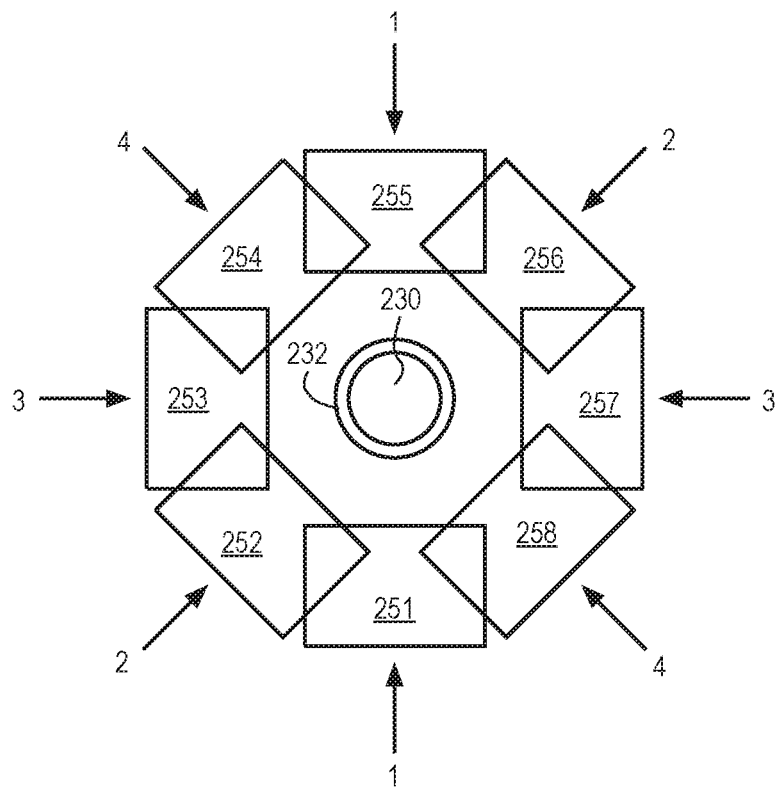
FIG. 5 is an illustrative drawing representing spatial disposition of the eight x-ray projection images of FIGS. 4A-4D in accordance with some embodiments.

FIG. 5 is an illustrative drawing representing spatial disposition of the eight 2-D x-ray projection images 251-258 of FIGS. 4A-4D in accordance with some embodiments. Each 2-D x-ray projection image is produced by passing x-ray radiation, along a different beam path, through the tissue volume 230 within the working volume 232. It will be appreciated that the working volume 232 is approximately centered on the center axis of the end portion 126 generally in the middle of the multiple projections.

Figure 6:
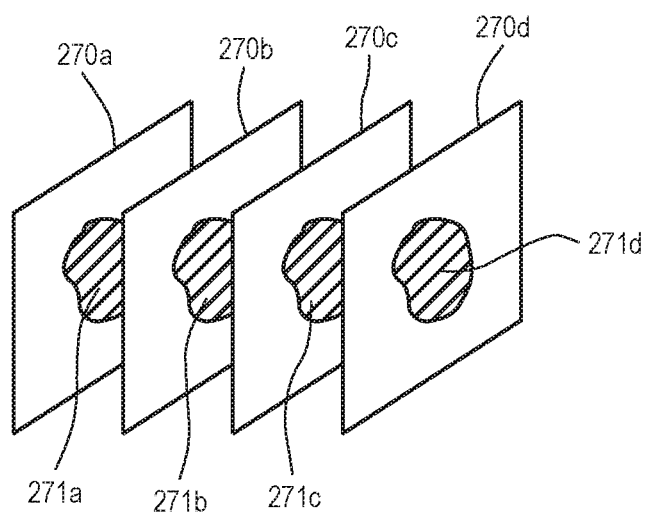
FIG. 6 is an illustrative drawing showing multiple tomosynthesis images generated by the visualization system based upon the x-ray projection images in accordance with some embodiments.

FIG. 6 is an illustrative drawing showing multiple tomosynthesis images 270a-270d generated by the visualization system 110 based upon the x-ray projection images 251-258 in accordance with some embodiments. More particularly, one or more processors are configured to convert the multiple 2-D projection images 251-258 to tomosynthesis images 270a-270d. It will be appreciated that although eight 2-D projection images and four tomosynthesis images are shown, a greater or lesser number of 2-D projection images and/or tomosynthesis images may be provided. Each example tomosynthesis image slice 271a-271d represents an image slice at a different Z-direction depth within the tissue volume 230. In the illustrated embodiment, a set of four tomosynthesis images 270a-270d are shown, although it will be appreciated that greater or fewer than four tomosynthesis images may be produced. In general, the spacing and the number of tomosynthesis images can be selected based on factors such as depth (e.g., in a Z-direction parallel to the axis 190), resolution, or a range of depths desired to be covered by the tomosynthesis images.

Tomosynthesis, also referred to as digital tomosynthesis (DTS), is a method for performing high-resolution limited-angle tomography. More specifically, tomosynthesis is a process used to reconstruct three dimensional (3-D) images based upon a limited set of two dimensional (2-D) scans. As used herein, the term "tomosynthesis image" or "tomosynthesis slice" refers to an image created using a number of 2-D projection images, where the number of 2-D projection images (input images) used to produce a tomosynthesis image is less than that needed for computed tomography (CT) image reconstruction. In some embodiments, producing tomosynthesis images from 2-D projections involves a technique commonly referred to as filtered back projection.

Generally speaking, each of the tomosynthesis images 270a-27d is constructed by determining a plurality of voxels, wherein each voxel is determined by considering indicia of x-ray beam attenuation associated with that voxel in each of the 2-D projection images 251-258. As used herein, a voxel (volumetric pixel or volumetric picture element) is a volume element, representing a value on a regular grid in three-dimensional space. Indicia of attenuation are accumulated from all 2-D projection images 251-258 to estimate the attenuation of a given voxel. The attenuation of a voxel is partly represented by an intensity value of its corresponding pixel in each projection image. By accumulating the values of pixels from all projection images 251-258 that correspond to a given voxel, the effect of attenuation at that voxel is constructively accumulated.

Determinations of pixel positions and values for each of the 2-D projection images 251-258 for use in voxel determinations can be made using known x-ray photogrammetry techniques and geometry calculations based upon the position of the (one or more) x-ray detector 260 relative to each of the x-ray emission devices 181-188, for example. It will be appreciated that the x-ray emission devices 181-188 are disposed within an anatomical lumen and that the detector 260 typically is disposed outside of the body, although in some embodiments, an x-ray detector may be disposed within a body lumen in a spaced relation to one or more x-ray emission devices.

The relative positions of the emission devices 181-188 and the detector(s) 260 can be readily determined. For example, as explained above, in some embodiments, an EM sensor system 136 and/or a shape sensor system 138 can be used to determine the position and orientation of the end portion 126 relative to the interface 122. For example, a location of the interface 122 is known, and therefore a location of the end portion 126 relative to the interface 122 can be determined to within an acceptable amount of precision. As explained below, small errors in sensed location of the end portion 126 may arise due to natural body motion such as breathing, for example. Referring to FIG. 2A, a position and orientation of the detector 260 relative to the interface 122 can be determined, for example, through physical dimensions and physical disposition, relative to the interface 122, of structures 261 on which the detector 260 is mounted, for example. These determined positions and orientations of the end portion 126 and the detector 260 can be used, for example, to align the one or more detector 260 with the emission devices 181-188 so as to capture x-ray radiation emitted by the devices 181-188. In some embodiments, particularly where tomosynthesis is employed, the (one or more) detector 260 is disposed to capture multiple x-ray radiation beams 241-248 that diverge from each other following their incidence upon a region of the body.

In practice, blurring of reconstructed the tomosynthesis images 270a-27d may result since voxels may be accumulated in a non-constructive fashion. Various methods can be performed to address this blurring. In some embodiments, tomosynthesis images can be de-blurred by performing back projection combined with filtering. De-blurred tomosynthesis images generated based on filtered back projection can be based on inverse of Radon transform using the back-projection theorem, for example. Tomosynthesis techniques are well known to persons of ordinary skill in the art and will not be further described herein. See, for example, T. Gomi et al., X-ray digital linear tomosynthesis imaging, J. Biomedical Science and Engineering, 2011, 4, 443-453, published online June 2011 (www.SciRP.org/journal/jbise/). Also see, for example, U.S. Pat. No. 7,532,705, filed Apr. 10, 2007, entitled, "System and Method for Localizing a Target for Radiotherapy based on Digital Tomosynthesis", and U.S. Pat. No. 7,711,087, filed Apr. 7, 2006, entitled, "Patient Setup using Tomosynthesis Techniques," which are expressly incorporated herein in their entirety by this reference.

Similarity Comparison Between Tomosynthesis Image and 2-D Reference Images

Figure 7:
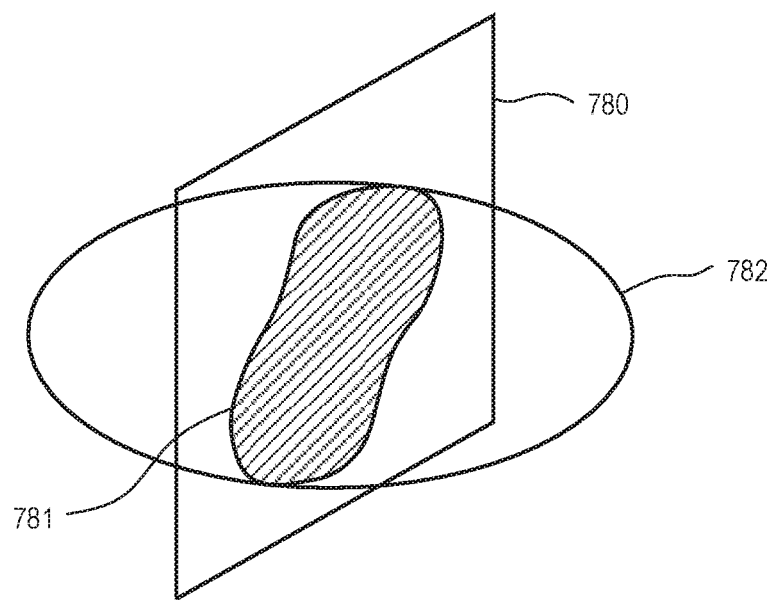
FIG. 7 is an illustrative drawing representing a 2-D reference image slice selected from a 3-D reference computed tomography image for matching with one or more tomosynthesis image slices in accordance with some embodiments.

FIG. 7 is an illustrative drawing representing a 2-D reference image slice 780 selected from a 3-D reference computed tomography image 782 that include a feature 781, such as an anatomical landmark, for matching with one or more tomosynthesis image slices in accordance with some embodiments. The 3-D reference computed tomography (CT) image 782, which is sometimes referred to as a "planning" CT image, is obtained for a portion of a patient's body during a diagnostic session, for example, in which the patient is diagnosed, or in a treatment planning session in which a treatment plan is determined, for example. In some embodiments, the 3-D reference CT image 782 can be obtained by using a CT machine (not shown) to deliver diagnostic radiation energy towards the patient at a multiplicity of angles so as to generate image data at different angles, which are then processed to reconstruct a three-dimensional CT image. Computed tomography is a well-known technique to persons of ordinary skill in the art and will not be further described herein.

In some embodiments, one or more processors are configured to compare one or more of the tomosynthesis images 270a-270d with a 2-D reference image slice 780 to determine an offset between a detected and predicted poses of the end portion 126. Hereinafter, an instrument pose that is determined using the tracking system 135 shall be referred to as a "predicted" pose. A thickness of the 2-D reference image slice 780 can be selected to be approximately the same as the depth resolution of the tomosynthesis images 270a-270d, thus making the 2-D reference image slice 780 and tomosynthesis images 270a-270d more compatible for comparison. In particular, the display system 111 can be used to display a reference image slice 780 and one or more tomosynthesis images 270a-270d. A determination is made as to one or more 2-D reference images that best match one or more of the tomosynthesis images. Estimation then can be made as to an offset between a matching 2-D reference image and the tomosynthesis images. It will be appreciated that the location within the patient's body of landmarks within the 2-D reference image are known with precision since the 2-D reference images are taken from the 3-D image information produced using a precision technique such as CT.

More particularly, based upon such comparison, an estimated offset can be determined between the detected and predicted end portion poses.

Figure 8:
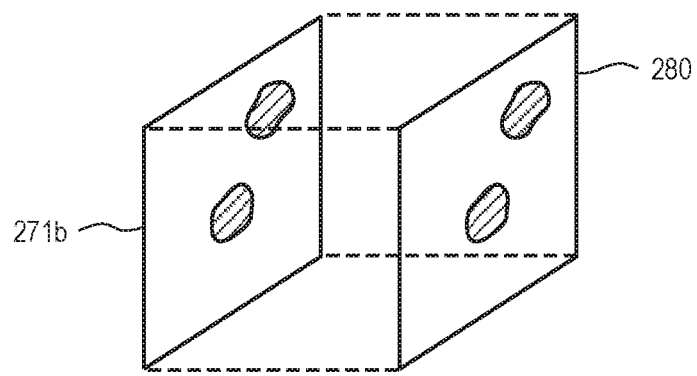
FIG. 8 is an illustrative drawing representing a detected tomosynthesis image and a 2-D reference image for comparison in accordance with some embodiments.

FIG. 8 is an illustrative drawing representing a detected tomosynthesis image 270b and a 2-D reference image 280 for comparison in accordance with some embodiments. Landmarks such as bone or soft tissue volumes or another fiducial represented in multiple 2-D reference images can be compared with landmarks represented in the tomosynthesis images in order to identify the best match.

Figure 9:
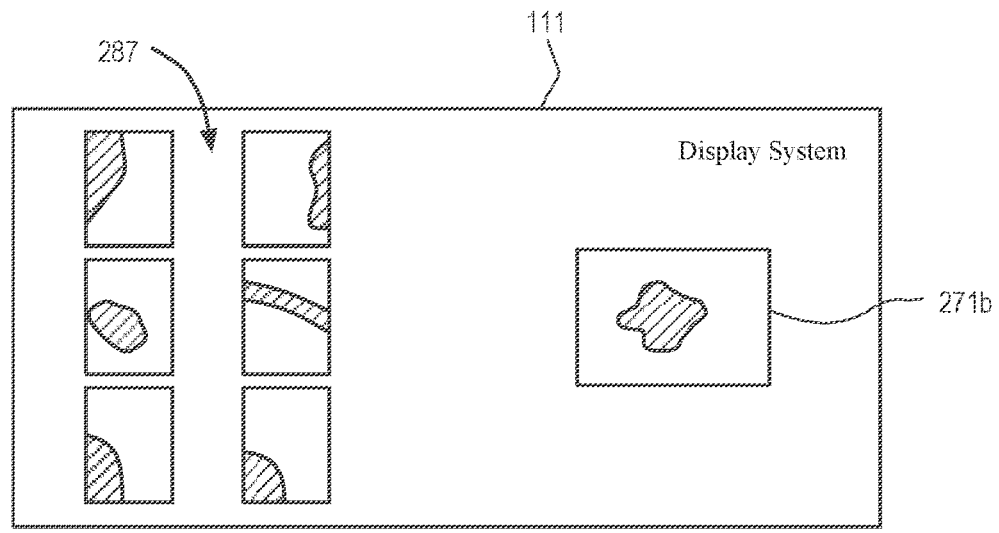
FIG. 9 is an illustrative drawing of an example screen display showing multiple 2-D reference slices alongside a selected tomosynthesis slice in accordance with some embodiments.

FIG. 9 is an illustrative simplified drawing of an example screen display showing multiple 2-D reference slices 287 alongside a selected tomosynthesis slice 271b in accordance with some embodiments. The visualization system 110 displays, on the display system 111, one or more tomosynthesis images representing the determined actual working volume together with one or more 2-D reference images so that a physician can make an assessment as to which 2-D reference image best matches the tomosynthesis images. The physician can thereby make a better determination of an actual current location of the working volume within a patient's body, and therefore, make a better determination of the position and/or orientation of the end portion 126 to bring an intended target tissue volume into alignment with the working volume. In other words, a physician or other operator can determine an offset between determined and predicted positions of the working volume through comparison of one or more tomosynthesis images with one or more 2-D reference images. It will be appreciated that although multiple different 2-D reference slices 287 are shown in FIG. 9, in an alternative embodiment, reference slices may be displayed individually in sequence as a physician pans across 2-D reference slice data or as the physician scrolls through the data, for example.

Similarity Comparison Between 2-D Projected Images and 2-D Reference Images

Figure 10:
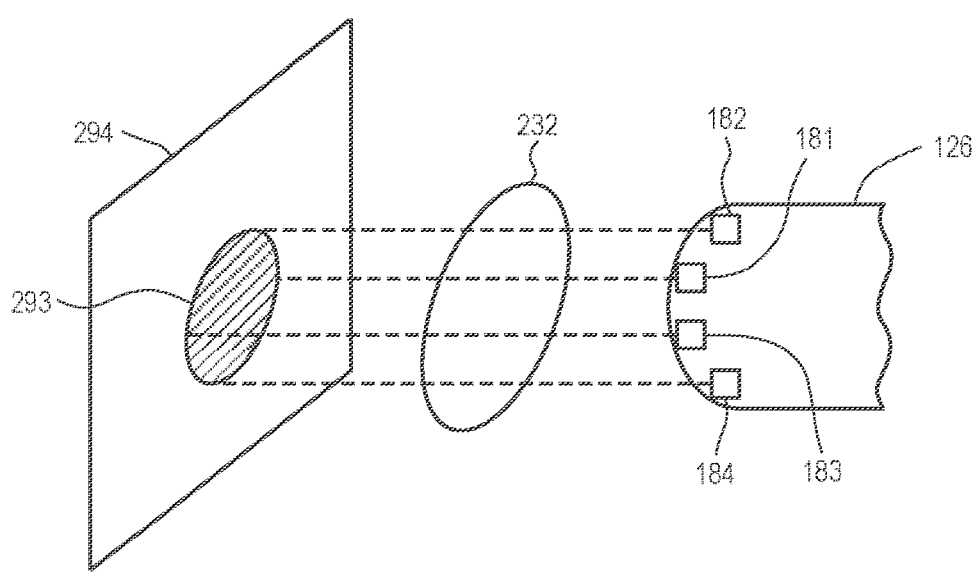
FIG. 10 is an illustrative drawing of an alternative embodiment of the end portion in which the emission sources are arranged to emit x-ray radiation in a direction generally parallel to the central axis of the end portion in accordance with some embodiments.

FIG. 10 is an illustrative drawing of an alternative embodiment of the end portion 126 in which the emission devices 181-184 are arranged to emit x-ray radiation beams in a direction generally parallel to the center axis of the end portion 126. The parallel x-ray radiation beams 290 penetrate the working volume 232, and a 2-D projection image 294 that includes feature 293 is captured by the detector 260 aligned with the x-ray radiation beams 290. In some embodiments, the projection image 294 is displayed using the display system 111, which can be viewed by a physician or other operator for comparison the 2-D projection image 294 with one or more 2-D reference slices. The position and/or orientation and/or shape of the instrument 104 can be changed as needed to more accurately navigate the instrument 104 within the patient's body and/or to align the working volume 232 with an intended target tissue volume, for example.

Emission Devices Configured to Intersect Displaced from the End Portion

Figure 11:
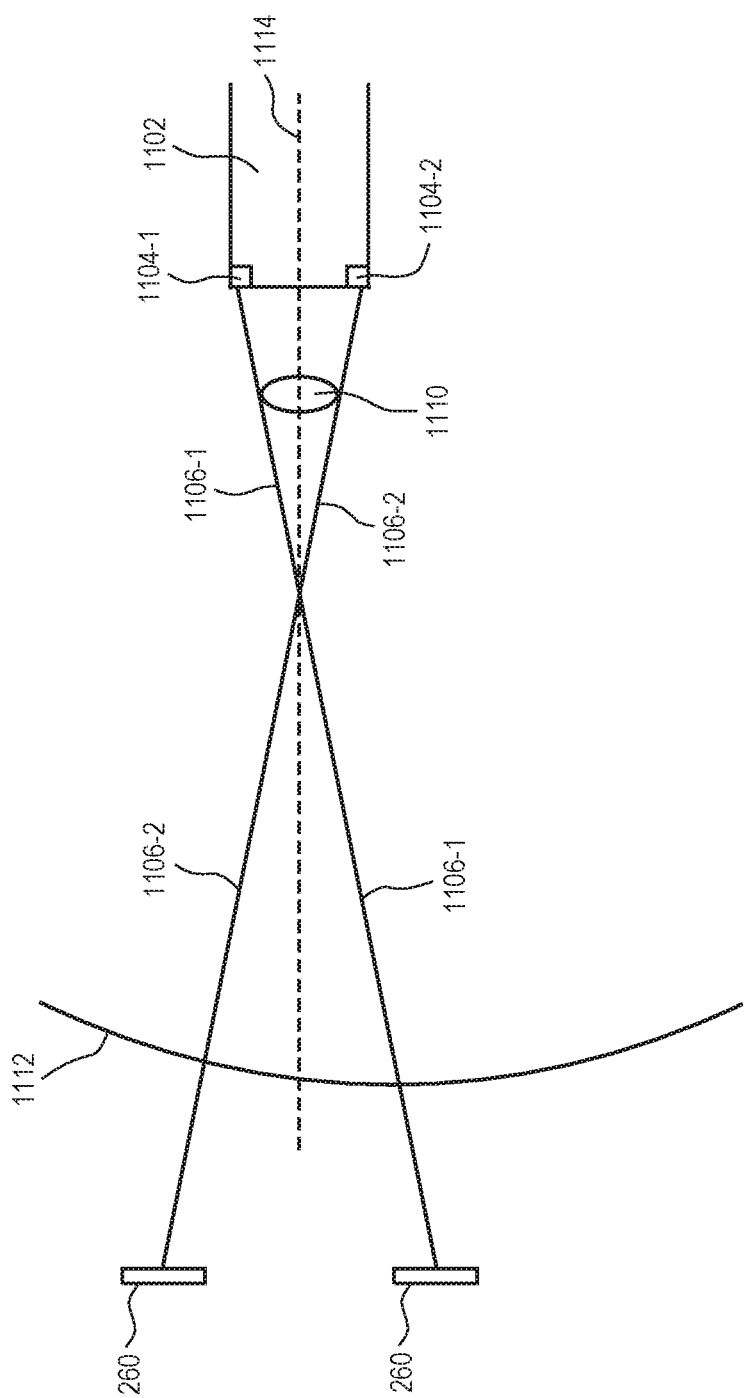
FIG. 11 is an illustrative drawing representing an alternative embodiment showing an end portion of a flexible medical instrument having x-ray emission devices configured to emit x-ray beams that intersect body tissue at a location that is displaced from a working volume.

FIG. 11 is an illustrative drawing representing an alternative embodiment showing an end portion 1102 having x-ray emission devices 1104-1, 1104-2 (only two shown) configured to emit x-ray beams 1106-1, 1106-2 that intersect body tissue a location that is displaced from a working volume 1110. One or more detector 260 is disposed outside of the patient's body 1112 to capture the beams 1106-1, 1106-2. The beams 1106-1, 1106-2 are configured so as to intersect with tissue that is aligned with an axis 1114 of the end portion 1102. Thus, 2-D projection images produced by the beams 1106-1, 1106-2 represent a viewpoint of a portion of body tissue aligned with the axis 1114 of the end portion 1102. It will be appreciated that the process described with reference to FIG. 11 can use the captured x-ray image information to identify and correct discrepancies between detected and predicted end portion poses.

Machine-Implemented Process to Compare Field Emission Images with Reference Images In some embodiments, one or more processors are configured to compare detected x-ray image information with reference x-ray image information to determine the actual position and orientation of an instrument end portion 126 within a patient's body. There can be a discrepancy or error, albeit a small one, between an actual pose and a predicted pose of the end portion 126. Such an error may result from the dynamic nature of certain anatomic structures such as the lungs or the heart. For example, inhalation and exhalation change the position and size of the bronchial passageways of the lung. Alternatively, the error may result from tissue deformation caused by the presence of the surgical instrument 104 within the anatomic passageways. In some situations, even a small discrepancy between predicted and actual position and/or orientation of the end portion 126 can be problematic, particularly if the instrument 104 is navigating through narrow or closely spaced anatomical passages or if a target tissue volume is especially small. Moreover, some target tissue volumes may be on the order of one millimeter in diameter or less, for example. As a consequence, the instrument 104 may sometimes become located within the wrong passage. Alternatively, for example, a discrepancy between the predicted and determined end portion pose can result in an intended target tissue volume not being disposed within the actual working volume. As a result of such discrepancy, the effector 132 may not be properly aligned to obtain a tissue sample from the intended target volume or to deliver a therapy or medicine to the intended target volume, for example.

Figure 12:
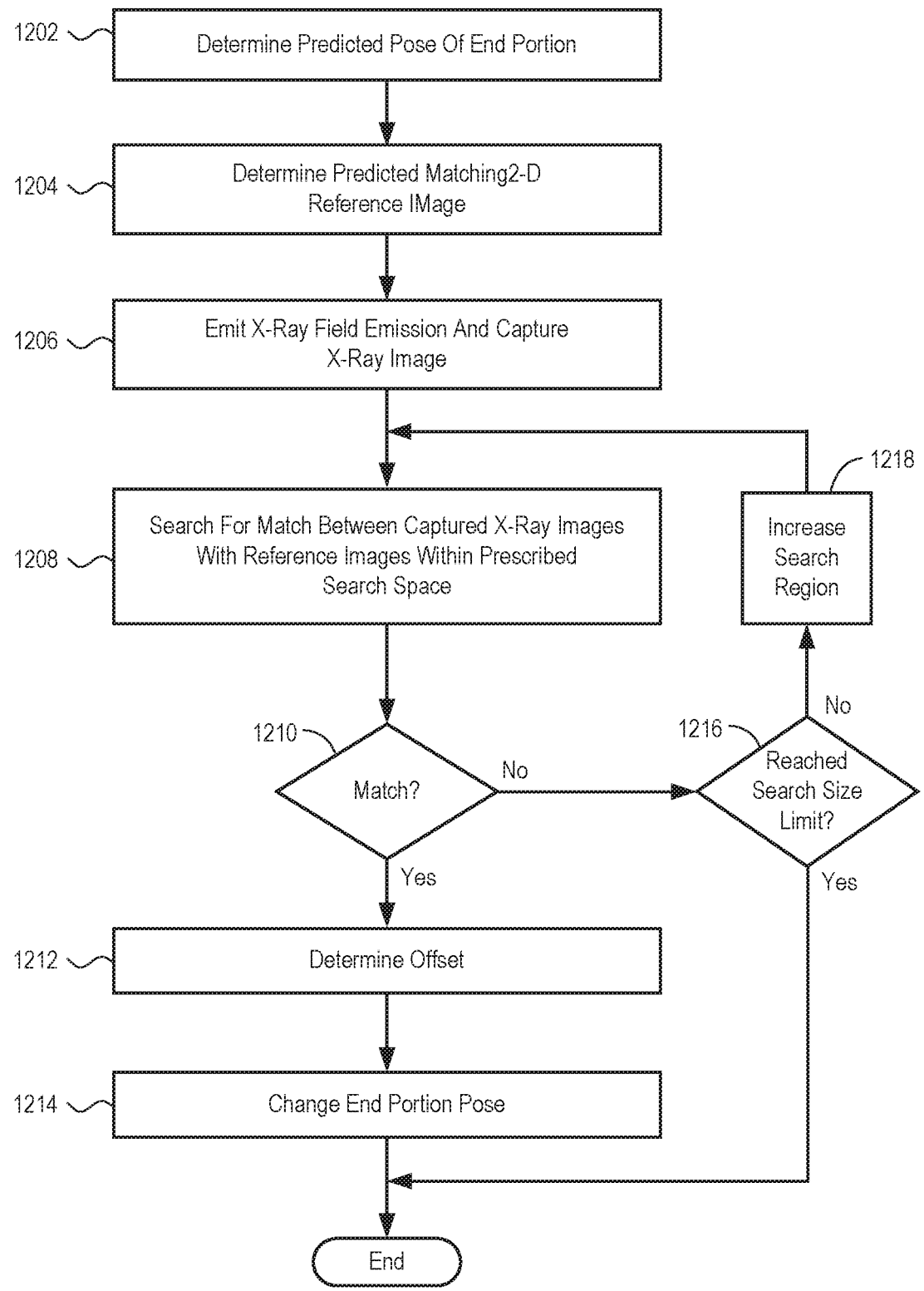
FIG. 12 is an illustrative flow diagram representing a process search for similarity between detected 2-D x-ray images and one or more 2-D reference x-ray images in accordance with some embodiments.

FIG. 12 is an illustrative flow diagram representing a process to search for similarity between detected 2-D x-ray images and one or more 2-D reference x-ray images in accordance with some embodiments. Operation 1202 configures one or more processors to determine a predicted position and orientation of the end portion 126. A sensed position and orientation of the end portion 126 within a patient's body are determined using the tracking system 135. In accordance with some embodiments, the electromagnetic (EM) sensor system 136 and the shape sensor system 138 can be used for determining the approximate position, orientation, speed, pose, and/or shape of the end portion 126. In addition, the image capture element 134 can be used to provide a visual indication of the approximate position of the end portion 126 from a perspective internal to the patient's body. U.S. patent application Ser. No. 13/893,040, filed on May 13, 2013, entitled "Systems and Methods for Registration of a Medical Device Using a Reduced Search Space," which is expressly incorporated herein in its entirety by this reference, discloses further details of a system and method for tracking a medical device within a patient anatomy during a medical procedure.

Operation 1204 configures one or more processors to determine a predicted matching 2-D reference image that corresponds to the predicted position and orientation of the end portion 126. The predicted matching 2-D reference image can be extracted from the 3-D reference information. A predicted x-ray beam path along the axis 190 of the end portion 126 disposed in the predicted position and orientation is used to identify and select the predicted 2-D reference image, which includes x-ray attenuation information corresponding to a portion of the patient's body from a viewpoint along that predicted path. In some embodiments, the x-ray attenuation information includes an attenuation pattern that is indicative of anatomical structures that the x-ray radiation has passed through en route to detection.

Operation 1206 configures one or more processors to configure the x-ray emission devices to emit x-ray radiation along a path that is incident upon a patient tissue. The x-ray emission path, which extends between the devices 181-188 and the detector 260, includes the working volume 232. The detector 260 captures 2-D projection images that contain x-ray attenuation information indicative of structures disposed along the emission path. Since there may be some discrepancy between the actual and predicted pose of the end portion 126, some adjustment of the position of the detector 260 may be needed to capture the emitted radiation. The location of the predicted 2-D reference frame can be used as a predictor of the x-ray emission path in making such adjustments.

Operation 1208 configures one or more processors to search for similarity between detected 2-D image information and 2-D reference image information obtained from the 3-D reference image information. The detected 2-D image information may comprise 2-D projection information or tomosynthesis information. In some embodiments, the search may involve configuring the control system 116 to perform an automated comparison of the detected 2-D image information and the 2-D reference image information. In particular, x-ray attenuation information from the detected 2-D image information is compared with x-ray attenuation information from the 3-D reference image information to identify a 2-D reference image that has sufficient similarity to the detected 2-D image to determine that there is a match. More particularly, the control system 116 is configured to identify a best match between the detected 2-D image information and one or more 2-D reference images. The predicted matching 2-D reference image can be used as a starting point within the 3-D image data for the similarity search. In embodiments, the search can cover some prescribed region within the 3-D image data about the predicted matching 2-D reference image. Alternatively, or in addition to the automated search, a surgeon or other technician may use the display system 111 to display both detected 2-D image information and 2-D reference image information for visual comparison to find a best match.

Decision operation 1210 configures one or more processors to determine whether a match is identified within the search region based upon a prescribed threshold level of similarity between the detected image information and 2-D reference image. Such match determination can be performed automatically through configuration of the control system 116 or can be performed manually through visual observation using display system 111. In response to a determination by decision operation 1210 that a match is identified, operation 1212 determines an estimated offset between actual and predicted poses of the end portion 126. Operation 1214 configures one or more processors to change a pose of the end portion 126 based at least in part upon the estimated offset. The change in end portion pose may be achieved manually through user actuation of the manipulator assembly 102 while receiving visual cues in the form of detected and reference x-ray images on the visualization system 110, for example. The process ends following the change in end portion pose.

In response to a determination by decision operation 1210 that no a match is identified within the search region, decision operation 1216 configures one or more processors to determine whether to increase the search region. In some embodiments, the search region may be increased incrementally up to some prescribed limit. In response to a determination to increase the search region, the operation 1218 configures one or more processors to enlarge the search region and directs the control flow of the process 1200 back to operation 1208. In response to a determination by decision operation 1216 to not increase the search region, operation 1218 reports an error and the process 1200 ends.

Examples of Different End Position Pose Offsets

Figure 13A:
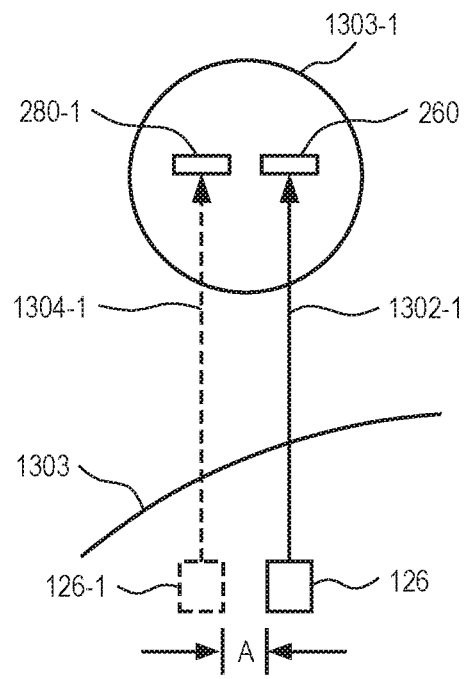
FIGS. 13A-13B are illustrative drawings showing two different example offsets between predicted and actual poses of the end portion of the flexible medical instrument in accordance with some embodiments.
Figure 13B:
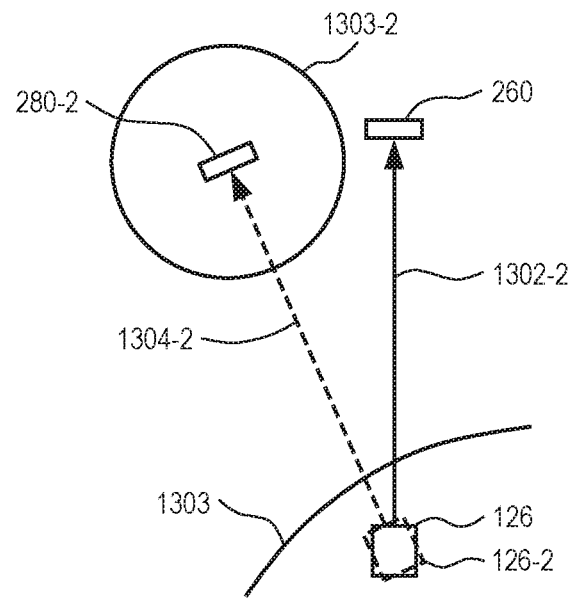

FIGS. 13A-13B are illustrative drawings showing two different offsets between predicted and actual poses of the end portion 126 of the medical instrument in accordance with some embodiments. FIG. 13A shows the predicted and detected positions of the end portion 126 offset by a distance "A". The end portion 126 disposed within a patient's body 1303 in a pose in which detected x-ray beams that follow a first emission path 1302-1 and that produce detected 2-D image information that is captured by the detector 260. Dashed lines 126-1 represent a predicted pose of the end portion 126 in which first predicted x-ray beams indicated by dashed lines follow a first predicted path 1304-1 that corresponds to a predicted 2-D reference image. Operation 1204 (FIG. 12) can be used to determine the predicted 2-D reference image 280, as explained above. In accordance with operation 1208, a search is conducted within a search region of 3-D image information, indicated by dashed lines 1303-1, to identify a best match between the detected image data and the reference image data.

FIG. 13B shows the predicted and detected poses of the end portion 126 offset by an angle "B". Dashed lines 126-2 represent a predicted pose of the end portion 126 in which second predicted x-ray beams follow a second predicted path 1304-2 that corresponds to a predicted 2-D reference image. Operation 1204 (FIG. 12) can be used to determine the predicted 2-D reference image, as explained above. In accordance with operation 1208, a search may be conducted within a search region of 3-D image information, which is indicated by dashed lines 1303-2, to identify a best match between the detected image data and the reference image data.

Anatomical Examples

Figure 14A:
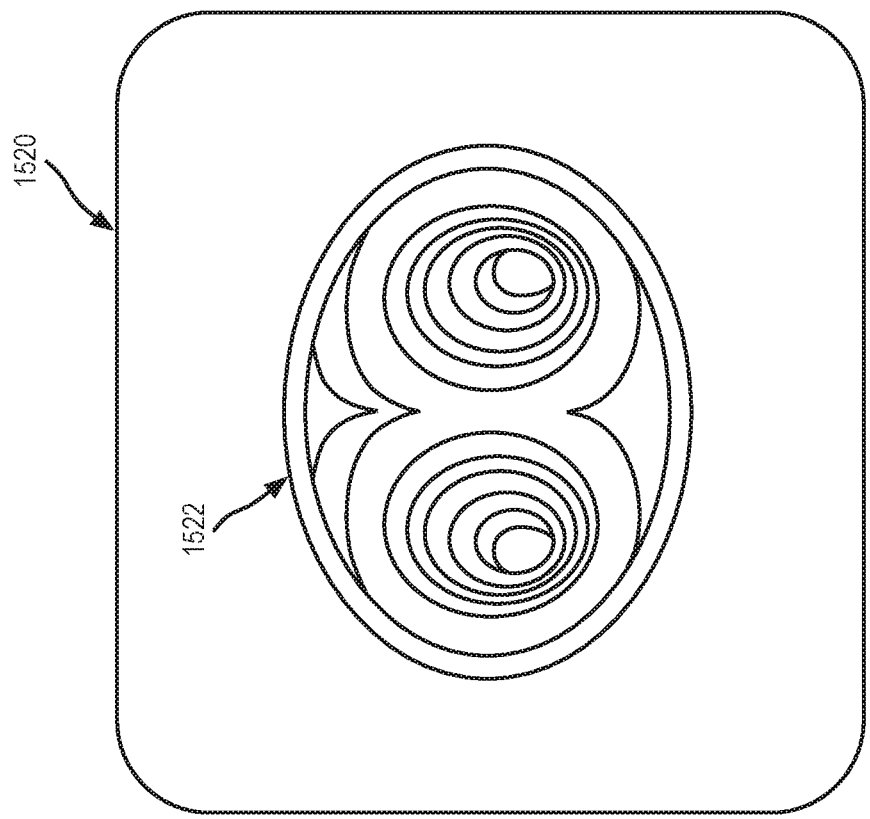
FIG. 14A is an illustrative drawing representing a composite image including an image of a human lung, from a viewpoint external to the lung, registered with an instrument image of a flexible instrument in accordance with some embodiments.

FIG. 14A is an illustrative drawing representing a composite image 1400 including an image 1402 of a human lung 1404, from a viewpoint external to the lung 1404, registered with an instrument image 1406 of a flexible instrument, such as the flexible instrument 120, in accordance with some embodiments. The image 1402 of the lung 1404 may be generated from preoperatively recorded images or may be generated concurrently during the surgical procedure. The composite image 1400 may be displayed via display system 111. As the instrument 120 is advanced through bronchial passageways 1408 of the lung 1404, information from the tracking system 135 and/or the visualization system 110 can be used to register the instrument image 1406 with the lung image 1402. The image 1402 of the lung 1404 may change, for example, to depict the lung 1404 in a state of inspiration or expiration. The instrument image 1406 may change to depict the advancement or withdrawal of the instrument 120 through the bronchial passageways 1408. In this example, a target tissue volume "X" is the intended target of a surgical procedure.

It will be appreciated that visual navigation within bronchial passages can be impractical due to mucous or other opaque fluids. Also, visual identification of the target tissue X volume may be impossible when such volume is disposed in an interstitial location not directly accessible to a bronchial passage. Moreover, sonic position sensing may not be practical because the instrument body 124 may be within a volume containing air or other fluid and not in contact with actual tissue.

Figure 15:
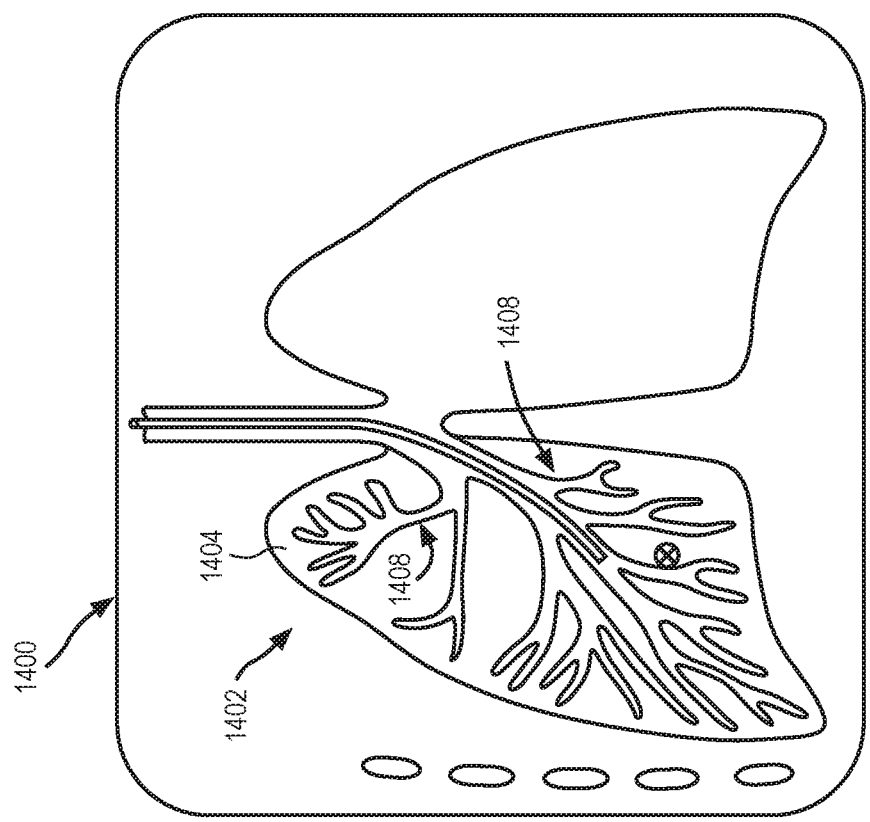
FIG. 15 is an illustrative drawing representing an internal image of a portion of the human lung of FIGS. 14A-14C depicting a region of the lung from the viewpoint along a Z-axis of the end portion the instrument flexible medical instrument poses in accordance with some embodiments.

FIG. 15 is an illustrative drawing representing an internal image 1520 of the human lung 1404 depicting a region 1522 of the lung 1404 from the viewpoint along a center of the end portion 126 the instrument 120 in accordance with some embodiments. The image 1520 may be a concurrent visual image taken using image capture element 134 during the surgical procedure by the instrument 120 while located in the depicted portion of the lung 1404. More specifically, the image 1520 may be captured by the visualization system 110. Alternatively, the image 1520 may be a preoperatively recorded image selected based upon the location of the tip of the instrument 120 as determined by the tracking system 135.

Figure 14B:
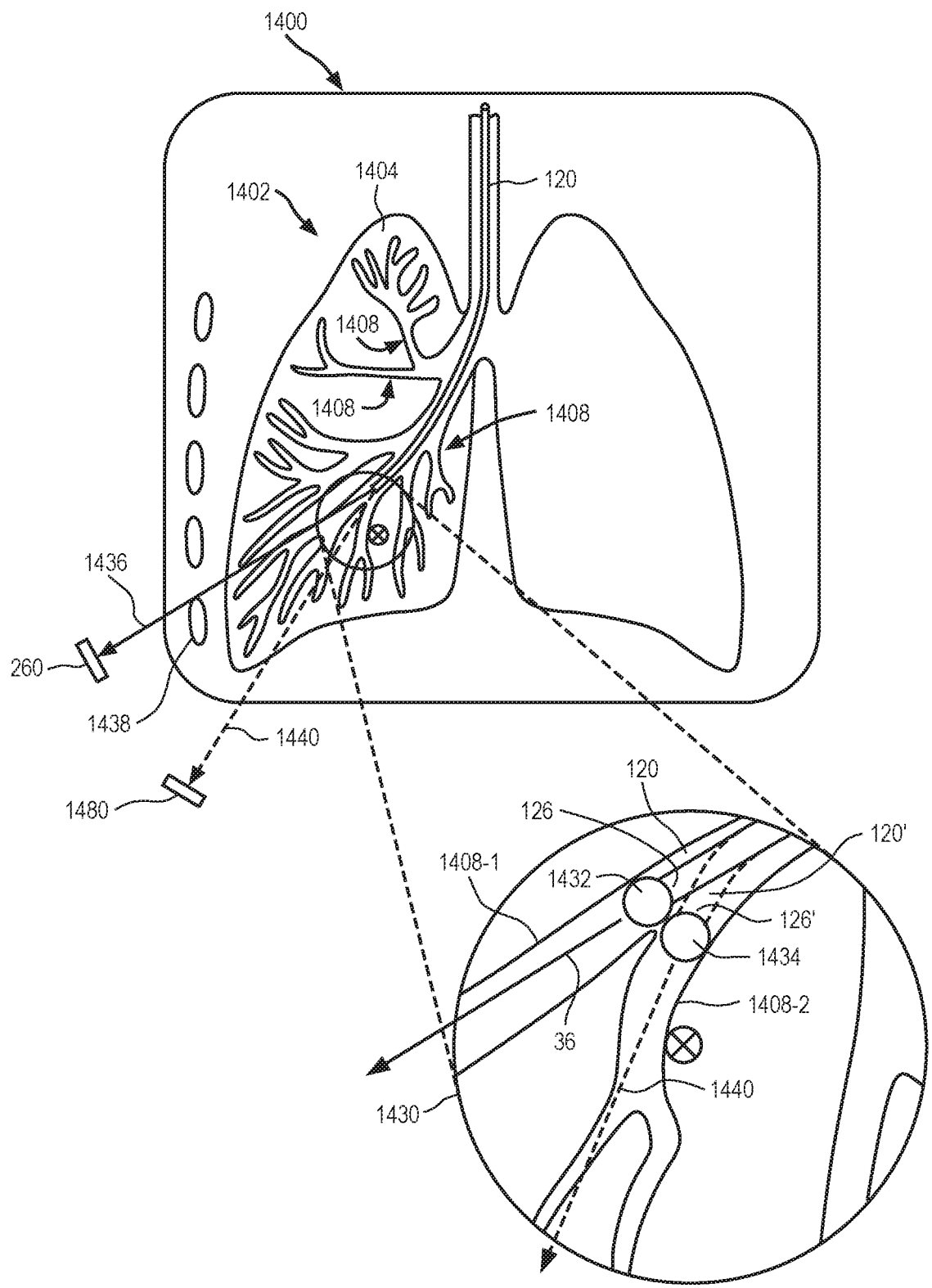
FIG. 14B shows the composite image of FIG. 14A and also shows a first example discrepancy between first detected and predicted flexible medical instrument poses in accordance with some embodiments.

FIG. 14B is an illustrative drawing showing an example of an instrument heading down the wrong anatomical passage. More particularly, FIG. 14B shows the composite image 1400 of FIG. 14A and also shows a first example discrepancy between first detected (actual) and predicted poses of the end portion 126 and corresponding detected (actual) and predicted working volume locations 1432, 1434 in accordance with some embodiments. FIG. 14B includes an enlarged view 1430 of a portion of the lung 1404 that includes first and second bronchial passages 1408-1, 1408-2, respectively. The end portion 126 is shown disposed at an entry to the first bronchial passage 1408-1. The actual working volume 1432 is shown adjacent the end portion 126. The target tissue volume X is disposed adjacent to a wall of the second bronchial passage 1408-2. Thus, the end portion 126 is erroneously headed down the wrong passage. A sensed position of the instrument 120 and its end portion 126 are indicated by dashed lines 120' and 126', respectively.

Still referring to FIG. 14B, a sensed pose of the instrument 120 end portion 126 indicated by dashed lines 120', 126' is determined in accordance with operation 1202 (FIG. 12). A predicted 2-D reference image 1480 is determined based upon predicted x-ray emission path 1440 in accordance with operation 1204.

The end portion 126 mounted emission devices 181-188 emit x-ray radiation 1436 that is captured by the detector 260 in accordance with operation 1206. The x-ray radiation 1436 is attenuated by lung tissue and other body structures, such as a rib 1438, disposed between the emission devices 181-188 and the detector 260. The detected x-ray image information is compared with 2-D reference x-ray image information from a 3-D reference image source. The predicted 2-D reference image 1480 can be used as a starting point in a search for a match. The detected (actual) pose of the end portion 126 can be changed to align with the predicted pose indicated by dashed lines 120', 126'.

Figure 14C:
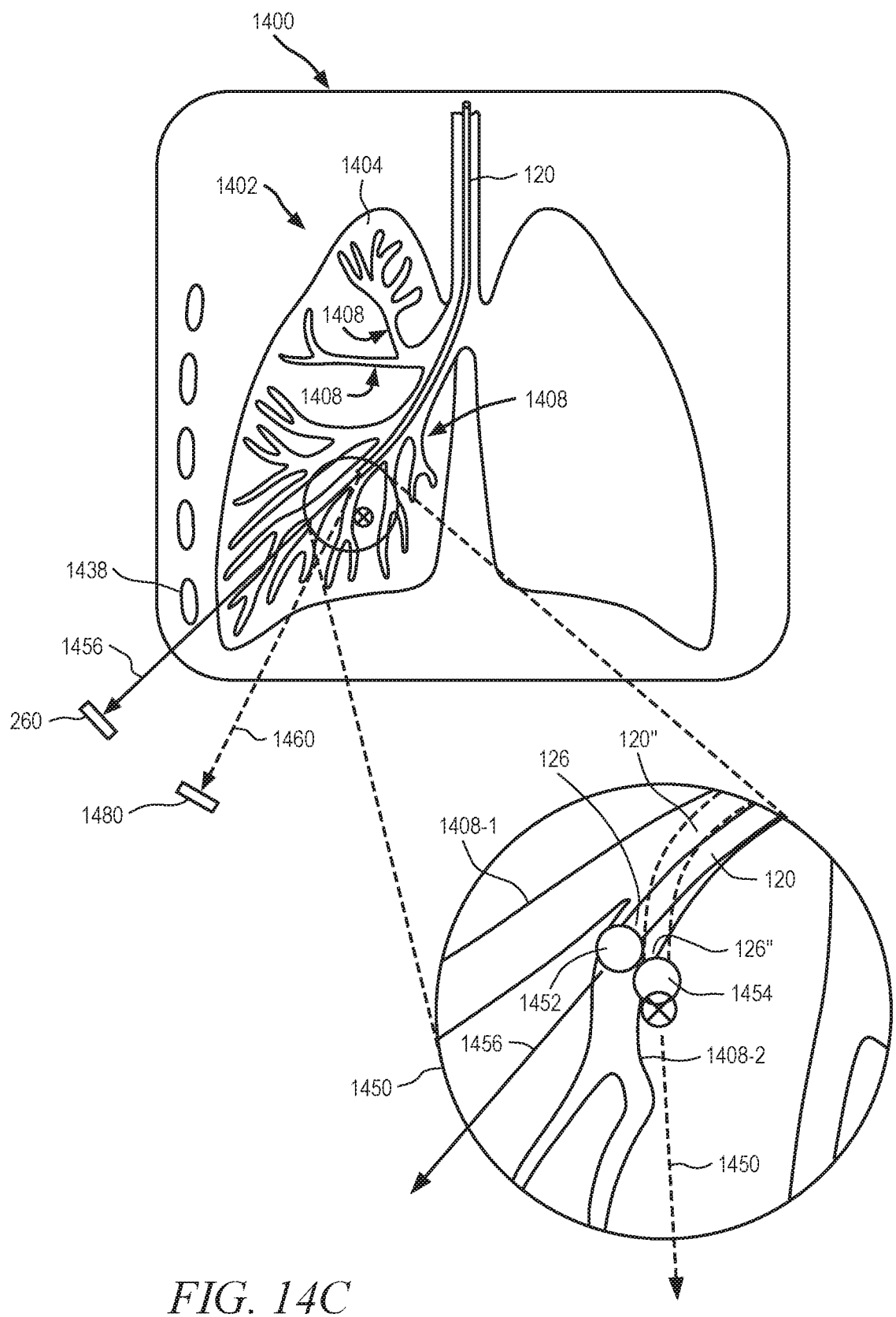
FIG. 14C shows the composite image of FIG. 14A and also shows a second example discrepancy between second detected and predicted flexible medical instrument poses in accordance with some embodiments.

FIG. 14C is an illustrative drawing showing an example of an instrument that is misaligned with respect to an intended target tissue volume. More particularly, FIG. 14C shows the composite image 1400 of FIG. 14A and also shows a second example discrepancy between second detected (actual) and predicted poses of the end portion 126 and corresponding detected (actual) and predicted working volume locations 1452, 1454 in accordance with some embodiments. FIG. 14C includes an enlarged view 1450 of a portion of the lung 1404 that includes the first and second bronchial passages 1408-1, 1408-2, respectively. The end portion 126 is shown disposed within the second bronchial passage 1408-2. However, the actual working volume 1454 adjacent the end portion 126 does not encompass any portion of the target tissue volume X. A sensed position of the instrument 120 and its end portion 126 is indicated by dashed lines 120" and 126", respectively. It can be seen that in this example, the predicted working volume location 1454 does overlap with the target tissue volume X. Thus, it can be seen that there is a discrepancy between locations of the actual and predicted working volumes.

Continuing to refer to FIG. 14C, a sensed pose of the instrument 120 end portion 126 indicated by dashed lines 120", 126" is determined in accordance with operation 1202. A predicted 2-D reference image 1490 is determined based upon predicted x-ray emission path 1460 in accordance with operation 1204. The end portion 126 mounted emission devices 181-188 emit x-ray radiation 1456 that is captured by the detector 260 in accordance with operation 1206. The x-ray radiation 1456 is attenuated by lung tissue and other body structures, such as a rib 1438, disposed between the emission devices 181-188 and the detector 260. The detected x-ray image information is compared with 2-D reference x-ray image information from a 3-D reference image source. The predicted 2-D reference image 1490 can be used as a starting point in a search for a match. The detected (actual) pose of the end portion 126 can be changed to align with the predicted pose indicated by dashed lines 120" and 126".

Computer Hardware and Storage Devices

Figure 16:
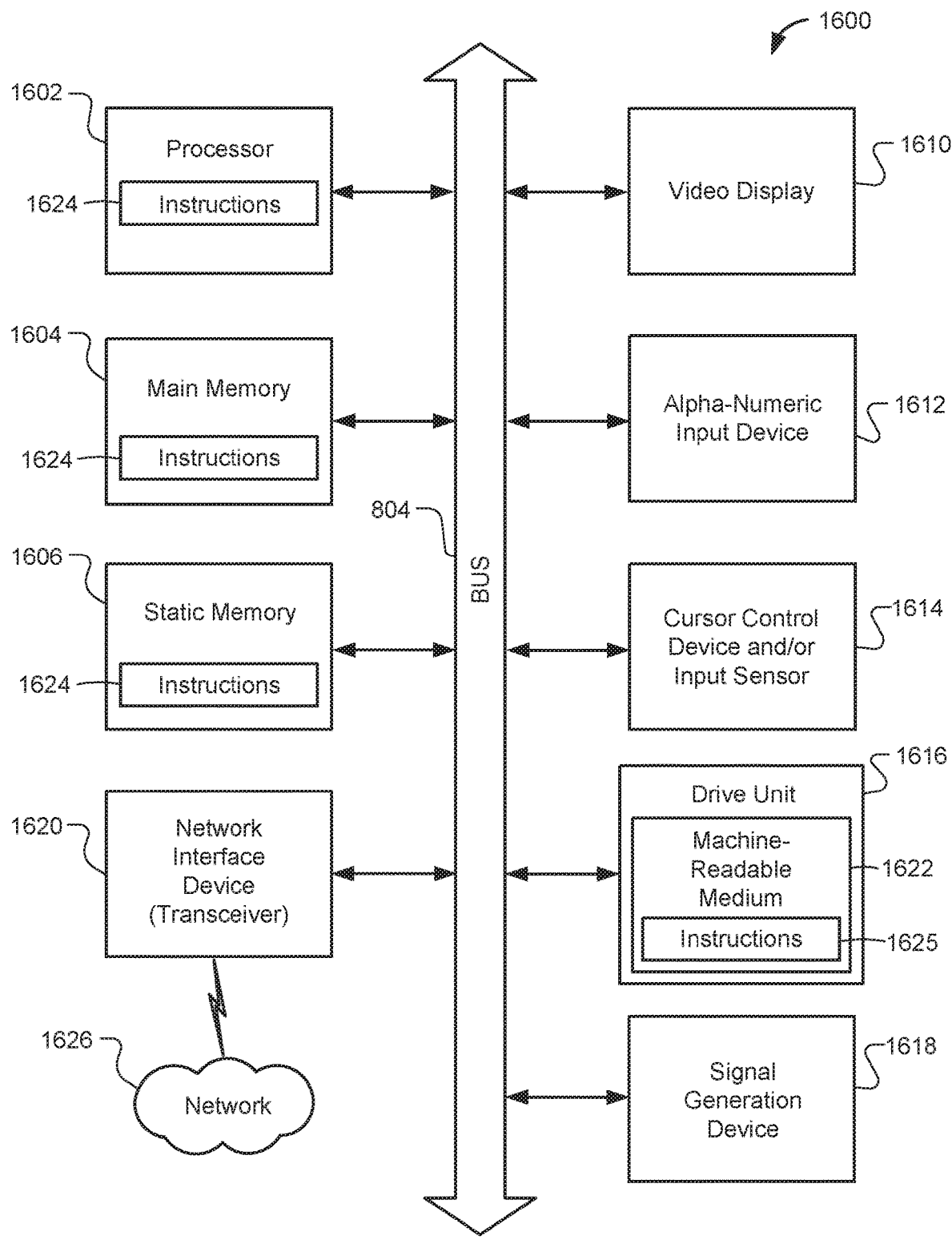
FIG. 16 shows an illustrative diagrammatic representation of a more particularized computer system to implement the generalized computer system of FIG. 16.

FIG. 16 shows an illustrative diagrammatic representation of a more particularized computer system 1600, in an example form, controller 116 and display system in accordance with some embodiments. The computer system 1600 can be configured to implement, for example, the control system 116 and the display system 111. In alternative embodiments, the computer system 1600 operates as a standalone device or may be connected (e.g., networked) to other machines. In a networked deployment, the computer system 1600 may operate in the capacity of a server or a client machine in server-client network environment, or as a peer machine in a peer-to-peer (or distributed) network environment. The computer system 1600 may be a server computer, a client computer, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine (i.e., computer system 1600) is illustrated, the term "machine" shall also be taken to include any collection of machines that individually or jointly execute a set (or multiple sets) of instructions to perform any one or more of the methodologies discussed herein.

The example computer system 1600 includes a processor 1602 (e.g., a central processing unit (CPU), a graphics processing unit (GPU), or both), a main memory 1604 and a static memory 1606, which communicate with each other via a bus 1608. The computer system 1600 may further include a video display unit 1610 (e.g., liquid crystal display (LCD), organic light emitting diode (OLED) display, touch screen, or a cathode ray tube (CRT)) that can be used to display positions of the surgical instrument 104 and flexible instrument 120, for example. The computer system 1600 also includes an alphanumeric input device 1612 (e.g., a keyboard, a physical keyboard, a virtual keyboard using software), a cursor control device or input sensor 1614 (e.g., a mouse, a track pad, a trackball, a sensor or reader, a machine readable information reader, bar code reader), a disk drive unit 1616, a signal generation device 1618 (e.g., a speaker) and a network interface device or transceiver 1620.

The disk drive unit 1616 includes a non-transitory machine-readable storage device medium 1622 on which is stored one or more sets of instructions 1624 (e.g., software) embodying any one or more of the methodologies or functions described herein, such as the processes of FIGS. 12 and 13A-13B. The instructions 1624 may also reside, completely or at least partially, within the main memory 1604, static memory 1606 and/or within the processor 1602 during execution thereof by the computer system 1600, the main memory 1604 and the processor 1602 also constituting non-transitory machine-readable storage device media. The non-transitory machine-readable storage device medium 1622 also can store an integrated circuit design and waveform structures.

The instructions 1624 may further be transmitted or received over a network 1626 via the network interface device or transceiver 1620.

While the machine-readable storage device medium 1622 is shown in an example embodiment to be a single medium, the term "machine-readable medium," "computer readable medium," and the like should be taken to include a single medium or multiple media (e.g., a centralized or distributed database, and/or associated caches and servers) that store the one or more sets of instructions 1624. The term "machine-readable medium" shall also be taken to include any medium that is capable of storing, encoding or carrying a set of instructions for execution by the machine and that cause the machine to perform any one or more of the methodologies of the present disclosure. The term "machine-readable medium" shall accordingly be taken to include, but not be limited to, solid-state memories, optical and magnetic media, and carrier wave signals.

It will be appreciated that, for clarity purposes, the above description describes some embodiments with reference to different functional units or processors. However, it will be apparent that any suitable distribution of functionality between different functional units, processors or domains may be used without detracting from the present disclosure. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Although the present disclosure has been described in connection with some embodiments, it is not intended to be limited to the specific form set forth herein. One skilled in the art would recognize that various features of the described embodiments may be combined in accordance with the present disclosure. Moreover, it will be appreciated that various modifications and alterations may be made by those skilled in the art without departing from the spirit and scope of the present disclosure.

In addition, in the foregoing detailed description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the detailed description, with each claim standing on its own as a separate embodiment.

The foregoing description and drawings of embodiments in accordance with the present invention are merely illustrative of the principles of the inventive subject matter. Therefore, it will be understood that various modifications can be made to the embodiments by those skilled in the art without departing from the spirit and scope of the inventive subject matter, which is defined in the appended claims.

Although the systems and methods of this disclosure have been illustrated for use in the connected bronchial passageways of the lung, they are also suited for navigation and treatment of other tissues, via natural or surgically created connected passageways, in any of a variety of anatomical systems including the digestive system, colon, the intestines, the kidneys, the brain, the heart, the circulatory system, or the like. The methods and embodiments of this disclosure are also suitable for non-surgical applications.

Thus, while certain exemplary embodiments of the invention have been described and shown in the accompanying drawings, it is to be understood that such embodiments are merely illustrative of and not restrictive on the broad inventive subject matter, and that the embodiments of the invention not be limited to the specific constructions and arrangements shown and described, since various other modifications may occur to those ordinarily skilled in the art.

What is claimed is:

1. A method, comprising:
   determining a predicted pose of an elongate medical device within a patient anatomy using shape data from a shape sensor of the elongate medical device;
   extracting a plurality of reference images from 3-D reference information, wherein the plurality of reference images includes a predicted reference image corresponding to the predicted pose of the elongate medical device;
   capturing an x-ray image of the patient anatomy, wherein the captured x-ray image includes captured x-ray attenuation information;
   searching the plurality of reference images for a closest matching reference image to the captured x-ray image; and
   determining an offset between the captured x-ray image and the closest matching reference image.

2. The method of claim 1, wherein the 3-D reference information includes reference x-ray attenuation information, and wherein the searching for a closest matching reference image between the captured x-ray image and the one of the plurality of reference images comprises comparing the captured x-ray attenuation information with the reference x-ray attenuation information.

3. The method of claim 1 further comprising:
   determining an adjustment of the elongate medical device based on the determined offset.

4. The method of claim 1 further comprising:
   emitting, by an x-ray emission device of the elongate medical device, an x-ray beam, wherein the x-ray image is generated by the x-ray beam.

5. The method of claim 1, wherein the searching for a closest matching reference image between the captured x-ray image and the one of the plurality of reference images comprises:
   determining a first search area including a subset of the plurality of reference images, wherein the first search area is based on the predicted reference image; and
   comparing the captured x-ray image to the plurality of reference images within the first search area.

6. The method of claim 5, wherein the comparing the captured x-ray image to the plurality of reference images comprises:
   determining a second search area by enlarging the first search area when the captured x-ray image does not match one of the plurality of reference images in the first search area within a threshold; and
   comparing the captured x-ray image to the plurality of reference images within the second search area.

7. The method of claim 1, wherein the searching for a closest matching reference image between the captured x-ray image and the one of the plurality of reference images comprises automatically searching, by a control system, for the closest matching reference image between the captured x-ray image and the one of the plurality of reference images.

8. The method of claim 1, wherein the searching for a closest matching reference image between the captured x-ray image and the one of the plurality of reference images comprises:
   receiving, by a control system, a user input corresponding to a selection of the one of the plurality of reference images; and
   determining a match between the captured x-ray image and the one of the plurality of reference images based on the received user input.

9. A system, comprising:
   an elongate medical device configured to be inserted into a patient anatomy, the elongate medical device comprising:
      a flexible body including a proximal portion and a distal portion; and
      an x-ray emitter configured to emit an x-ray beam;
   an x-ray emission detector configured to detect the x-ray beam emitted by the x-ray emitter; and
   a control system configured to:
      extract a plurality of reference images from 3-D reference information of the patient anatomy;
      capture, by the x-ray emission detector, an x-ray image of the patient anatomy;
      search for a closest matching reference image between the captured x-ray image and one of the plurality of reference images; and
      determine an offset between the captured x-ray image and the closest matching reference image.

10. The system of claim 9, wherein the x-ray emitter includes a carbon nanotube.

11. The system of claim 9, wherein the x-ray emitter includes a plurality of field emission x-ray devices positioned within the distal portion of the flexible body.

12. The system of claim 9, wherein the x-ray emitter includes a plurality of field emission x-ray devices positioned about a circumference of the flexible body.

13. The system of claim 12, wherein the plurality of field emission x-ray devices are oriented to emit electrons along different intersecting beam paths.

14. The system of claim 9, wherein the captured x-ray image includes captured x-ray attenuation information of the patient anatomy and the 3-D reference information includes reference x-ray attenuation information of the patient anatomy, and wherein searching for a closest matching reference image between the captured x-ray image and the one of the plurality of reference images comprises comparing the captured x-ray attenuation information with the reference x-ray attenuation information.

15. The system of claim 9, wherein the elongate medical device further comprises at least one of a shape sensor or an EM sensor, and wherein the control system is further configured to determine a predicted pose of the elongate medical device using data from at least one of the shape sensor or the EM sensor.

16. The system of claim 15, wherein:
- the plurality of reference images includes a predicted reference image corresponding to the predicted pose of the elongate medical device; and
- the searching for a closest matching reference image between the captured x-ray image and the one of the plurality of reference images comprises determining a first search area including a subset of the plurality of reference images, the first search area being based on the predicted reference image.

17. The system of claim 16, wherein the searching for a closest matching reference image between the captured x-ray image and the one of the plurality of reference images further comprises comparing the captured x-ray image to the plurality of reference images within the first search area.

18. The system of claim 9, wherein the control system is further configured to determine a predicted pose of the elongate medical device by determining a predicted position of the elongate medical device using image data.

19. A method, comprising:
- determining a predicted pose of an elongate medical device within a patient anatomy;
- extracting a plurality of reference images from 3-D reference information, wherein the plurality of reference images includes a predicted reference image corresponding to the predicted pose of the elongate medical device;
- emitting, by an x-ray emission device of the elongate medical device, an x-ray beam;
- capturing an x-ray image of the patient anatomy, wherein the x-ray image is generated by the x-ray beam, and wherein the captured x-ray image includes captured x-ray attenuation information;
- searching the plurality of reference images for a closest matching reference image to the captured x-ray image; and
- determining an offset between the captured x-ray image and the closest matching reference image.

* * * * *